US008822496B2

(12) United States Patent
Haefner et al.

(10) Patent No.: US 8,822,496 B2
(45) Date of Patent: Sep. 2, 2014

(54) DOSAGE REGIMENS FOR HCV COMBINATION THERAPY

(75) Inventors: Carla Haefner, Neu-Ulm (DE); Gerhard Steinmann, Erbach (DE); Jerry O. Stern, New Fairfield, CT (US); Chan-Loi Yong, Brookfield, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 460 days.

(21) Appl. No.: 12/913,323

(22) Filed: Oct. 27, 2010

(65) Prior Publication Data

US 2011/0268700 A1   Nov. 3, 2011

Related U.S. Application Data

(60) Provisional application No. 61/256,516, filed on Oct. 30, 2009.

(51) Int. Cl.
| | | |
|---|---|---|
| A01N 43/42 | (2006.01) |
| A01N 43/78 | (2006.01) |
| A01N 43/36 | (2006.01) |
| A61K 31/47 | (2006.01) |
| A61K 31/425 | (2006.01) |
| A61K 31/40 | (2006.01) |
| A61K 38/00 | (2006.01) |
| A61K 38/21 | (2006.01) |
| A61K 38/14 | (2006.01) |
| A61K 31/4709 | (2006.01) |
| A61K 31/7056 | (2006.01) |

(52) U.S. Cl.
CPC ........... *A61K 31/4709* (2013.01); *A61K 38/212* (2013.01); *A61K 31/7056* (2013.01); *Y10S 514/894* (2013.01)
USPC ........... 514/314; 514/312; 514/371; 514/423; 514/424; 514/4.3; 514/588; 514/894; 424/85.4; 424/85.7

(58) Field of Classification Search
None
See application file for complete search history.

(56) References Cited

U.S. PATENT DOCUMENTS

| | | | |
|---|---|---|---|
| 4,247,479 A | 1/1981 | Berthold |
| 5,908,621 A | 6/1999 | Glue et al. |
| 6,172,046 B1 | 1/2001 | Albrecht |
| 6,177,074 B1 | 1/2001 | Glue et al. |
| 6,299,872 B1 | 10/2001 | Albrecht et al. |
| 6,323,180 B1 | 11/2001 | Llinas-Brunet et al. |
| 6,403,564 B1 | 6/2002 | Ganguly et al. |
| 6,461,605 B1 | 10/2002 | Cutler et al. |
| 6,472,373 B1 | 10/2002 | Albrecht |
| 6,524,570 B1 | 2/2003 | Glue et al. |
| 6,608,027 B1 | 8/2003 | Tsantrizos et al. |
| 6,824,768 B2 | 11/2004 | Stalgis et al. |
| 6,849,254 B1 | 2/2005 | Brass et al. |
| 6,867,185 B2 | 3/2005 | Campbell et al. |
| 6,927,208 B1 | 8/2005 | Wenger et al. |
| 7,049,325 B2 | 5/2006 | Broka et al. |
| 7,141,574 B2 | 11/2006 | Beaulieu et al. |
| 7,173,004 B2 | 2/2007 | McPhee et al. |
| 7,189,844 B2 | 3/2007 | Gallou et al. |
| 7,375,218 B2 | 5/2008 | Gallou |
| RE40,525 E | 9/2008 | Llinas-Brunet et al. |
| 7,511,145 B2 | 3/2009 | Schmitz et al. |
| 7,514,557 B2 | 4/2009 | Busacca et al. |
| 7,576,079 B2 | 8/2009 | Beaulieu et al. |
| 7,582,770 B2 | 9/2009 | Tsantrizos et al. |
| 7,585,845 B2 | 9/2009 | Llinas-Brunet et al. |
| 7,642,235 B2 | 1/2010 | Llinas-Brunet et al. |
| 7,879,851 B2 | 2/2011 | Tsantrizos et al. |
| 7,893,084 B2 | 2/2011 | Beaulieu et al. |
| 7,939,667 B2 | 5/2011 | Llinas-Brunet et al. |
| 7,981,930 B2 * | 7/2011 | Nguyen et al. ................ 514/529 |
| 8,030,309 B2 | 10/2011 | Tsantrizos et al. |
| 8,067,438 B2 | 11/2011 | Llinas-Brunet et al. |
| 8,232,293 B2 | 7/2012 | Berkenbusch et al. |
| 8,399,484 B2 | 3/2013 | Huang et al. |
| 2003/0224977 A1 | 12/2003 | Llinas-Brunet et al. |
| 2004/0248779 A1 | 12/2004 | Dersch et al. |
| 2005/0020503 A1 | 1/2005 | Llinas-Brunet et al. |
| 2005/0049187 A1 | 3/2005 | Brandenburg et al. |
| 2005/0075279 A1 | 4/2005 | Llinas-Brunet et al. |
| 2005/0080005 A1 | 4/2005 | Llinas-Brunet et al. |
| 2005/0112093 A1 | 5/2005 | Ette et al. |
| 2005/0129659 A1 | 6/2005 | Lu |
| 2005/0153877 A1 | 7/2005 | Miao et al. |

(Continued)

FOREIGN PATENT DOCUMENTS

| | | |
|---|---|---|
| JP | 2002519434 A | 7/2002 |
| JP | 2008514732 A | 5/2008 |

(Continued)

OTHER PUBLICATIONS

Clinical Trial NCT00774397 (Oct. 16, 2008), pp. 1-5.*
White et al., EASL 45$^{th}$ Annual Meeting, pp. 1-8.*
Kieffer et al. (2007), Hepatology, vol. 46, pp. 631-639.*
Beringer et al. "The aromatization and rearrangment of cyclic kentones. IV. substituted acetanilides from cyclohexenone oximines," Journal of the American Chemical Society, 1953 vol. 75, pp. 2635-2639.
Cziaky et al., "Synthesis of 2H-pyranol[2, 3-b]quinolines, Part I" Journal of Heterocyclic Chemistry, vol. 31 1994, pp. 701-705
Desheiko et al., "58 Treatment of Chronic Hepatitis C with Telaprevir in combination with Peginterferon-Alfa-2a with or without ribavirin: further interim analysis results of the prove2 study", J of Hepatology, 2008, vol. 48, pp. S26.

(Continued)

*Primary Examiner* — Christine J Saoud
*Assistant Examiner* — Jegatheesan Seharaseyon
(74) *Attorney, Agent, or Firm* — Michael P. Morris; Philip I. Datlow

(57) ABSTRACT

The present invention relates to therapeutic combinations comprising (a) Compound (1), or a pharmaceutically acceptable salt thereof, as herein described, (b) an interferon alfa and (c) ribavirin and particular regimens for administering this combination. Compound (1) is a selective and potent inhibitor of the HCV NS3 serine protease. The present invention also relates to methods of using such therapeutic combinations for treating HCV infection or alleviating one or more symptoms thereof in a patient.

11 Claims, 3 Drawing Sheets

(56) References Cited

U.S. PATENT DOCUMENTS

| | | |
|---|---|---|
| 2005/0209135 A1 | 9/2005 | Busacca et al. |
| 2005/0222236 A1 | 10/2005 | Tsantrizos et al. |
| 2005/0267018 A1 | 12/2005 | Blatt et al. |
| 2005/0267151 A1 | 12/2005 | Busacca et al. |
| 2006/0009667 A1 | 1/2006 | Herweck et al. |
| 2006/0293320 A1 | 12/2006 | Schmitz et al. |
| 2007/0032488 A1 | 2/2007 | Botyanszki et al. |
| 2007/0196385 A1 | 8/2007 | Zahm |
| 2007/0202078 A1 | 8/2007 | Smith |
| 2007/0274951 A1 | 11/2007 | Tong et al. |
| 2008/0138316 A1 | 6/2008 | Cornu-Artis et al. |
| 2008/0177029 A1 | 7/2008 | Busacca et al. |
| 2010/0068182 A1 | 3/2010 | Huang et al. |
| 2010/0093792 A1 | 4/2010 | Berkenbusch et al. |
| 2011/0160149 A1 | 6/2011 | Chen et al. |
| 2011/0268700 A1 | 11/2011 | Haefner et al. |
| 2012/0135949 A1 | 5/2012 | Boecher et al. |

FOREIGN PATENT DOCUMENTS

| | | |
|---|---|---|
| JP | 2008525459 A | 7/2008 |
| WO | 03053349 | 7/2003 |
| WO | 2004094452 | 11/2004 |
| WO | 2004103996 A1 | 12/2004 |
| WO | 2005095403 | 10/2005 |
| WO | 2005116054 A1 | 12/2005 |
| WO | 2006018725 A1 | 2/2006 |
| WO | 2006039668 A2 | 4/2006 |
| WO | 2006071619 A1 | 7/2006 |
| WO | 2007014926 A1 | 2/2007 |
| WO | 2007129119 A1 | 11/2007 |
| WO | 2007150001 A1 | 12/2007 |
| WO | 2008005519 A1 | 1/2008 |
| WO | 2008070358 A2 | 6/2008 |
| WO | 2008121634 A2 | 10/2008 |
| WO | 2009005676 A2 | 1/2009 |
| WO | 2009005677 A2 | 1/2009 |
| WO | 2009014730 A1 | 1/2009 |
| WO | 2009020828 A1 | 2/2009 |
| WO | 2009021121 A2 | 2/2009 |
| WO | 2009039135 A1 | 3/2009 |
| WO | 2009099596 A2 | 8/2009 |
| WO | 2010031829 A1 | 3/2010 |
| WO | 2010033443 A1 | 3/2010 |
| WO | 2010033444 A1 | 3/2010 |
| WO | 2010042834 A1 | 4/2010 |
| WO | 2011053617 A1 | 5/2011 |
| WO | 2011112761 A1 | 9/2011 |
| WO | 2012041771 A1 | 5/2012 |

OTHER PUBLICATIONS

Fried et al.; Peginterferon Alfa-2a Plus Ribevirin for Chronic Hepatitis C Virus Infection: New England Journal of Medicine; Sep. 26, 2002; vol. 347; No. 13; pp. 975-982.

Gawley, R.E. The Beckmann reactions: rearrangement, elimination-additions, fragmentations and rearrangement-cyclizations. Organic Reactions 1986, 35, HCPLUS, Accession No. 2008:1383638.

Hezode et al., "Prove2 study: Treatment of chronic hepatitis C with telaprevir in combination with peginterferon-alfa-2a with or without ribavirin, interim analysis results", Gastroenterology, 2008, vol. 134, No. 4, Suppl. 1, pp. A755.

Jerry March; Advanced Organic Chemistry; 1992; 4th Edition; John Wiley and Sons: pp. 641-644.

Kwo, et al., "995 Interim results from HCV Sprint-1: RVR/EVR from Phase 2 study of Boceprevir plus Pegintrontm (Peginterferon Alfa-2B)/ribavirin in treatment-naive subjects with genotype-1 CHC", J. of Hepatology, 2008, vol. 48, p.S372.

Lawitz et al., Antiviral effects and safety of telaprevir, peginterferon alfa-2a, and ribavirin for 28 days in hepatitis C patients, J of Hepatology, 2008; vol. 49, pp. 163-169.

Liang et al.; HCV RNA in Patients With Chronic Hepatitis C Treated With Interferon-a; Journal of Medical Virology; 1993; vol. 40; pp. 69-75.

Manns et al.; Peginterferon alfa-2b plus ribavirin compared with interferon alfa-2b plus ribavirin for initial treatment of chronic hepatitis C: a ramdomised trial; The Lancet; Sep. 22, 2001; vol. 358; pp. 958-965.

Newman et al., "An improved aromatization of a tetralone oximes to N-(-1-naphthyl)acetamides," Journal of Organic Chemistry, 1973, vol. 38, No. 23, pp. 4073-4074.

Poynard et al.; Randomised trial of interferon a2b plus ribavirin for 48 weeks or for 24 weeks versus interferon a2b plus placebo for 48 weeks for treatment of chronic infection with hepatitis C virus; The Lancet; Oct. 31,1998; vol. 352-pp. 1426-1432.

Reichard et al.; Randomised, double-blind, placebo-controlled trial of interferon a-2b with and without ribavirin for chronic hepatitis C; The Lancet; Jan. 10, 1998; vol. 351, pp. 83-87.

Saneyoshi et al,; Syntheses and Properties of Several 4-Alkyl-or Arvlsulfonvleuinoline 1-Oxides; Chemcial & Pharmaceutical Bulletin, 1968, vol. 16; No. 7, pp. 1390-1394.

Schiff et al., "Role of interferon response during RE-treatment of null responders with boceprevir combination therapy: Results of Phase II trial", Gastroenterology, 2008, vol. 134, No. 4, Suppl. 1, pp. A755.

Shepherd et al., "2-bromo-3-methoxycyclohex-2-3none, a new reagent for the a-arylation of lactams," Journal of the Chemical Societer Perkin Transaction 1 Organic and Bio-Organic Chemistry, 1987, pp. 2153-2155.

Tamura, Y. A mild and efficient method for Semmler-Wolff aromatization; a versatile route to m-alkoxy-m-halo-, and m-thiocyanatoacetanilides. Synthesis 1980, 11, 887-9; HCPLUS, Accession No. 198:191859.

Wrobel; Silane-Mediated Direct Condensation of Nitroarenes with Cinnamyl-type Sulfones. The way to 2-Aryl-4-X-quinolines and Their Hetero Analogs; Tetrahedron; 54; 1998; pp. 2607-2618.

Koev et al., Antiviral interactions of an HCV polymerase, inhibitor with HVC protease inhibitor or interferon in vitro, Antiviral research, Jan. 14, 2007, vol. 73 No. 1, pp. 78-83, XP022575663.

Tan et al., 936 Combnation of the NS3/4A Protease Inhibitor ITMN-191 With the Allosteric NS5B Polymerase Inhibitor ITMN-8020 Enhances Replicon Clearance and Reduces the Emergence of Drug Resistant Variants, Journal of Hepatology, Apr. 1, 2009, vol. 50, pp. S340-S431, XP026138128.

Wyles et al., The Potential for Combination Treatment Using STAT-C Drugs, Current Hepatitis Reports, Current Science, Sep. 1, 2009, vol. 8 No. 1, pp. 27-34, XP019890556.

Zeuzem et al., Efficacy of the Protease Inhibitor BI 201335, Polymerase Inhibitor BI 207127, and Ribavirin in Patients With Chronic HCV Infection, Gastroenterology, Dec. 2011, vol. 141 No. 6, pp. 2047-2055, XP002664706.

International Search Report, Form PCT/ISA/210, and Written Opinion, Form PCT/ISA/237, for PCT Application PCT/US2010/054194 mailed Feb. 2, 2011.

Levin et al.; BI 201335, a Potent HCV NS3 protease Inhibitor, in treatment-naive and -experienced chronic HCV genotype-1 infection: genotypic and phenotypic analysis of the NS3 protease domain, Internet article: http://www.natap.org/2009/EASL/EASL_88.htm, Apr. 22, 2009, pp. 1-10, XP002617591.

Manns et al., Saftey and Antiviral Activity of BI 201335, A New HCV NS3 Protease Inhibitor, in Combination Therapy With Peginterferon Alfa 2A (P) and Ribavirin (R) Fro 28 Days in P+R Treatment-Experienced Patients With Chronic Hepatitis Genotype-1 Infection, Hepatology, Oct. 2008, vol. 48 No. 4, pp. 1151A-1152A, XP009143481.

Manns et al., Saftey and Antiviral Activity of BI 201335, A New HCV NS3 Protease Inhibitor, in Treatment-Naive Patients With Chronic Hepatitis C Genotype-1 Infection Given as Monotherapy and in Combination With Peginterferon Alfa 2A (P) and Ribavirin (R), Hepatology, Oct. 2008, vol. 48 No. 4, pp. 1133A, XP009143480.

McHutchison et al., Interferon Alfa-2b Alone or in Combination with Ribavirin as initial Treatment for Chronic Hepatitis C, New England Journal of Medicine, 1998, vol. 339 No. 21, pp. 1485-1492.

Lee et al., Treating chronic hepatitis C with pegylated interferon alfa-2a (40kD) and ribavirin in clinical practice, Aliment Pharmacol. Ther., 2006, vol. 23, pp. 397-408.

(56) References Cited

OTHER PUBLICATIONS

Manns et al., Potency, Safety, and Pharmacokinetics of the NS3/4A Protease Inhibitor BI201335 in Patients With Chronic HCV Genotype-1 Infection, Journal of Hepatology, vol. 54, No. 6, pp. 1114-1122, (2011).
Sulkowski et al., Silen-C1: Sustained Virologic Response (SVR) and Safety of BI201335 Combined With Peginterferon Alfa-2A and Ribavirin (P/R) in Treatment-Naive Patients With Chronic Genotype 1 HCV Infection, Journal of Hepatology, vol. 54, pp. S27, abstract 60 (2011).
Sane et al., Mechanisms of Isolated Unconjugated Hyperbilirubinemia Induced by the HCV NS3/4A Protease Inhibitor BI201335, Journal of Hepatology, vol. 54, pp. S488, Abstract 1236, (2011).
Pol et al., SVR and Pharmacokinetics of the HCV Protease Inhibitor BI201335 With Pegifn/RBV in HCV Genotype1 Patients With Compensated Liver Cirrhosis and Nonresponse to Previous Pegifn/RBV, Journal of Hepatology, vol. 54, pp. S486 Abstract 1231, (2011).
Yong et al. BI201335 Pharmacokinetics and Early Effect on Viral Load in HCV Genotype1 Patients, Journal of Hepatology, vol. 54, pp. S493, Abstract 1249, (2011).
Sulkowski et al., SILEN-C2: Early Antiviral Activity and Safety of BI 201335 Combined With Peginterferon Alfa-2A and Ribavirin (Pegifn/RBV) in Chronic HCV Genotype1 Patients With Nonresponse to Pegifn/RBV, Journal of Hepatology, vol. 52, pp. S462-S463, Abstract 1190 (2010).
Kukolj et al., BI 201335, A Potent HCV NS3 Protease Inhibitor, in Treatment-Naive and Experienced Chronic Hcv Genotype1 Infection. Genotypic and Phenotypic Analysis of the NS3 Protease, Journal of Hepatology, vol. 50, pp. S347, Abstract 954 (2009).
Sulkowski et al., SILEN-C2: Sustained Virologic Response (SVR) and Safety of BI201335 Combined With Peginterferon Alfa-2A and Ribavirin (P/R) in Chronic HCV Genotype-1 Patients With Non-Response to P/R, Journal of Hepatology, vol. 54, pp. S30, Abstract 66, 2011.
Amorosa et al.; New Frontiers of HCV therapy in HIV/HCV co-infection, Current Science Inc., vol. 7 No. 3, Aug. 2010, pp. 117-122. BI 201335 demonstrates potential to shorten HCV treatment duration while achieving high sustained virological response rates in difficult to treat patients, Nov. 2011, pp. 1-2 [Retrieved from the internet] http://www.boehringer-ingelheim.com/news/news_releases/press_releases/2011/08november20IIhcv.html.
Graham et al.; Influence of Human Immunodeficiency Virus Infection on the Course of Hepatitis C Virus Infection: A Meta-Analysis, Clinical Infectious Diseases, vol. 33 No. 4, Aug. 15, 2011, pp. 562-569.
Highleyman et al.: EASL: Once Daily BI 201335 Ups Response to Interferon for Hepatitis C, Apr. 15, 2011 Retrieved from the internet: URL:Http:/www.hivandhepatitis.com/hcv-treatment/experimental-hcv-drugs/2968-once-daily-bi201335-ups-response-to-interferon-for-hepatitis-c [retrieved on Nov. 9, 2011].
Highleyman et al: AASLD: All-Oral Combination of BI 201335, BI 207127 and Ribavirin Shows Good Efficacy at 12 Weeks, Dec. 1, 2011, pp. 1-3 Retrieved from the Internet: URL:www.hivandhepatitis.com/hepatitis-c/hepatitis-c-topics/hcv-treatment/3371-aasld-all-oral-combination-of- bi-201335-bi-207127-and-ribavirin-shows-good-efficacy-at-12-weeks.
Larrey et al; Rapid and strong antiviral activity of the non-nucleosidic NS5B polymerase inhibitor BI 207127 incombination with peginterferon alfa 2a and ribavirin, Journal of Hepatology, vol. 57, No. 1, Mar. 7, 2012, pp. 39-46.
Liu et al., New protease inhibitors for the treatment of chronic hepatitis C:a cost-effectiveness analysis. Annals of Internal Medicine 21, vol. 156, No. 4, Feb. 21, 2012, pp. 279-290.
Liu et al: New protease inhibitors for the treatment of chronic hepatitis C: a cost-effectiveness analysis, Annals of Internal Medicine, vol. 156, No. 4, Feb. 21, 2012, pp. 279-290.
Monto at al.; Lessons From HIV Therapy Applied to Viral Hepatitis Therapy: Summary of a Workshop, America Journal of Gastroenterology, vol. 105 No. 5, May 2010, pp. 989-1004.
Phase III Trial of B1 201335 in Treatment Naive (TN) and Relapser Hepatitis C Virus (HCV)-Human Immunodeficiency Virus (HIV) Coinfected Patients. Retrieved from the internet: URL:http://clinicaltrials.gov/archive/NCTO1399619/2012_03_06 [retrieved on Nov. 9, 2012].
Pol et al., 1231 SVR and Pharmacokinetics of the HCV Protease Inhibitor BI201335 With PEGIFN/RBV in HCV Genotype-1 Patients With Compensated Liver Cirrhosis and Non-Response to Previous PEGIFN/RBV, Journal of Hepatology, vol. 54, Mar. 1, 2011, p. S486.
Pol et al., Virological Response and Safety of BI 201335 Protease Inhibitor, Peginterferon Alfa 2A and Ribavirin Treatment of HCV Genotype-1 Patients With Compensated Liver Cirrhosis and Non-Response to Previous Peginterferon / Ribavirin, 60th Annual Meeting of the American Association for the Study of Liver Diseases (AASLD), Online Publication date Oct. 20, 2009.
Sulkowski el al., Silen-C2: Sustained Virologic Response (SVR) and Safety of BI201335 Combined With Peginterferon ALfa-2A and Ribavirin (P/R) in Chronic HCV Genotype-1 Patients With Non-Response to P/R, Apr. 1, 2011 Retrieved from the internet: URL:http://www1.easl.eu/eas12011/program/orals/330.htm.
Sulkowski et al.; 66 Silen-C2: Sustained Virologic Response (SVR) and Saftey of BI201335 Combined With Peginterferon Alfa-2A and Ribavirin (P/R) in Chronic HCV Genotype-1 Patients With Non-Response to P/R, Journal of Hepatology, vol. 54, Mar. 1, 2011, p. S30.
Sulkowski et al.; Silen-C1: Sustained Virologic Response (SVR) and Safety of BI201335 Combined With Peginterferon Alfa-2A and Ribavirin (P/R) in Treatment-Naive Patients With Cronic Genotype 1 HCV Infection, Apr. 1, 2011 Retrieved from the internet: URL:http://www1.easl.eu/eas12011/program/orals/324.htm.
Sulkowski et al: Treatment With the Second Generation HCV Protease Inhibitor BI201335 Results in High and Consistent SVR Rates—Results From Silen-C1 in Treatment-Naive Patients Across Different Baseline Factors, Hepatology, vol. 54, No. Suppl. 1, Oct. 2011, p. 473A.
Vachon et al.; BI-201335 Treatment of Hepatitis C Virus Serine Protease NS3/Non-Structural Protein 4A (NS4A) Inhibitor, Drugs of the Future, vol. 37 No. 2, Feb 1, 2012, pp. 99-109.
Zeuzem et al: High Sustained Virologic Response Following Interferon-Free Treatment of Chronic HCV GT1 Infection for 4 Weeks With HCV Protease Inhibitor BI201335, Polymerase Inhibitor BI207127 and Ribavi Rin, Followed by BI201335 and PEGIFN/Ribavirin—The Sound-C1 Study, Hepatology, Williams and Wilkins, Baltimore, MD, US, vol. 54, No. Suppl. 1, Nov. 2011, pp. 486A-487A.
Zeuzem et al: Strong Antiviral Activity and Safety of IFN-Sparing Treatment With the Protease Inhibitor BI201335, the HCV Polymerase Inhibitor BI207127 and Ribavirin in Patients With Chronic Hepatitis C, Hepatology, Williams and Wilkins, Baltimore, MD, US, vol. 52, No. Suppl, Oct. 1, 2010, pp. 876A-877A.
Zeuzem et al: Virologic Response to an Interferon-Free Regimen of BI201335 and BI207127, With and Without Ribavi Rin, in Treatment-Naive Patients With Chronic Genotype-1 HCV Infection: Week 12 Interim Results of the Sound-C2 Study, Hepatology, Williams and Wilkins, Baltimore, MD, US, vol. 54, No. Suppl. 1, Nov. 1, 2011, p. 1436A.
Benet et al., The Pharmacological Basis of Therapeutics, Goodmans & Gilmans textbook, 9th Edition, 1995, pp. 24-27.
McHutchison et al., Telaprevir for Previously Treated Chronic HCV Infection, New England Journal of Medicine, 2010, vol. 362, pp. 1292-1303.
Sulkowski et al.; Faldaprevir Combined With Peginterferon Alfa-2A and Ribavirin (P/R) in Treatment-Naive Patients With Chronic Genotype-1 HCV: Silen-C1 Trial, Hepatology, Jan. 31, 2013, pp. 1-39.
Asselah et al., Direct acting antivirals for the treatment of chronic hepatitis C, Liver International, 2012, vol. 32, Supp. 1 p. 88-102.
Brown et al., Progress towards improving antiviral therapy for hepatitis C with hepatitis C virus polymerase inhibitors. Part I: Nucleoside analogues, Expert Opinion on Investigational Drugs, Ashley Publications Ltd, London, Jun. 2009, vol. 18, No. 6, pp. 709-725.
Brown et al., Safety and Pharmacokinetics of PPI-461, a Potent new Hepatitis C virus (HCS) NS5A Inhibitor with Pan-Genotype Activity, Hepathology, 2010, vol. 52, No. 4, Suppl. S, pp. 879A-880A.

(56) References Cited

OTHER PUBLICATIONS

Chan et al., Discovery of thiophene-2-carboxylic acids as potent inhibitors of HCV NS5B polymerase and HCV subgenomic RNA replication. Part 2: Tertiary amides, Bioorg. & Med. Chem. Letters, 2004, vol. 14, p. 797-800.

Chatterji et al., The Isomerase Active Site of Cyclophilin A is Critical for Hepatitis C Virus Replication, Journal of Biological Chemistry, Jun. 2009, vol. 284, No. 25, pp. 16998-17005.

Kronenberger et al., Novel hepatitis C drugs in current trials, Clinics in Liver Disease, Saunders, PH Aug. 2008, vol. 12, No. 3, pp. 529-555.

Narjes et al., Discovery of (7 R)-14-Cyclohexyl-7-{[2-(dimethylamino)ethyl](methyl) amino}-7,8-dihydro-6 H-indolo[1,2-e][1,5]benzoxazocine-11-cyrboxylic Acid (MK-3281), a Potent and Orally Bioavailable Finger-Loop Inhibitor of the Hepatitis C Virus NS5B Polymerase, Journal of Medicinal Chemistry, Jan. 2011, vol. 54, No. 1, pp. 289-301.

Nettles et al., BMS-824393 is a Potent Hepatitis C Virus NS5A Inhibitor with Substantial Antiviral Activity when given as Monotherapy in Subjects with Chronic G1 HCV Infection, Hepatology, Oct. 2010, vol. 52. No. 4, Suppl. S, pp. 1203A-1204A.

O'Leary et al., Hepatitis C virus replication and potential targets for direct-acting agents, Therapeutic advances in gastroenterology, Jan. 2010, vol. 3, No. 1, pp. 43-53.

Schinazi et al., HCV drug discovery aimed at viral eradication, Journal of viral Hepatitis, Feb. 2010, vol. 17, No. 2, pp. 77-90.

Susser et al., Clonal analysis of mutations selected in the HCV NS3 protease domain of genotype 1 NOH-responders treated with boceprevier, J of Hepatology, 2008, vol. 48, Supp 2, p. S29.

* cited by examiner

DOSAGE REGIMENS FOR HCV COMBINATION THERAPY

TECHNICAL FIELD OF THE INVENTION

The present invention relates to therapeutic combinations comprising Compound (1) as herein described, an interferon alfa and ribavirin. The present invention also relates to methods of using such therapeutic combinations for treating HCV infection or alleviating one or more symptoms thereof in a patient. The present invention also relates to particular regimens for administering the therapeutic combinations. The present invention also provides kits comprising the therapeutic combinations of the present invention.

BACKGROUND OF THE INVENTION

Hepatitis C virus (HCV) infection is a global human health problem with approximately 150,000 new reported cases each year in the United States alone. HCV is a single stranded RNA virus, which is the etiological agent identified in most cases of non-A, non-B post-transfusion and post-transplant hepatitis and is a common cause of acute sporadic hepatitis. It is estimated that more than 50% of patients infected with HCV become chronically infected and 20% of those develop cirrhosis of the liver within 20 years.

Several types of interferons, in particular, alfa-interferons are approved for the treatment of chronic HCV, e.g., interferon-alfa-2a (ROFERON®-A), interferon-alfa-2b (INTRON®-A), consensus interferon (INFERGEN®), as well as pegylated forms of these and other interferons like pegylated interferon alfa-2a (PEGASYS®) and pegylated interferon alfa-2b (PEG-INTRON®). Most patients are unresponsive to interferon-alfa treatment, however, and among the responders, there is a high recurrence rate within 6 months after cessation of treatment (Liang et al., *J. Med. Virol.* 40:69, 1993).

Ribavirin, a guanosine analog with broad spectrum activity against many RNA and DNA viruses, has been shown in clinical trials to be effective against chronic HCV infection when used in combination with interferon-alfas (see, e.g., Poynard et al., *Lancet* 352:1426-1432, 1998; Reichard et al., *Lancet* 351:83-87, 1998), and this combination therapy has been approved for the treatment of HCV: REBETRON® (interferon alfa-2b plus ribavirin, Schering-Plough); PEGASYS®RBV® (pegylated interferon alfa-2a plus ribavirin combination therapy, Roche); see also Manns et al, *Lancet* 358:958-965 (2001) and Fried et al., 2002, *N. Engl. J. Med.* 347:975-982. However, even with this combination therapy the virologic response rate is still at or below 50%.

Furthermore, there are significant side-effects typically associated with such therapies. Ribavirin suffers from disadvantages that include teratogenic activity, interference with sperm development, haemolysis, fatigue, headache, insomnia, nausea and/or anorexia. Interferon alfa, with or without ribavirin, is associated with many side effects. During treatment, patients must be monitored carefully for flu-like symptoms, depression, rashes and abnormal blood counts. Patients treated with interferon alfa-2b plus ribavirin should not have complications of serious liver dysfunction and such subjects are only considered for treatment of hepatitis C in carefully monitored studies.

Certain interferon-containing combination therapies for treating HCV infection are also disclosed in the following U.S. Patent Application Publications: US 2005/0112093; US 2005/0129659; and US 2008/0138316.

The following Compound (1):

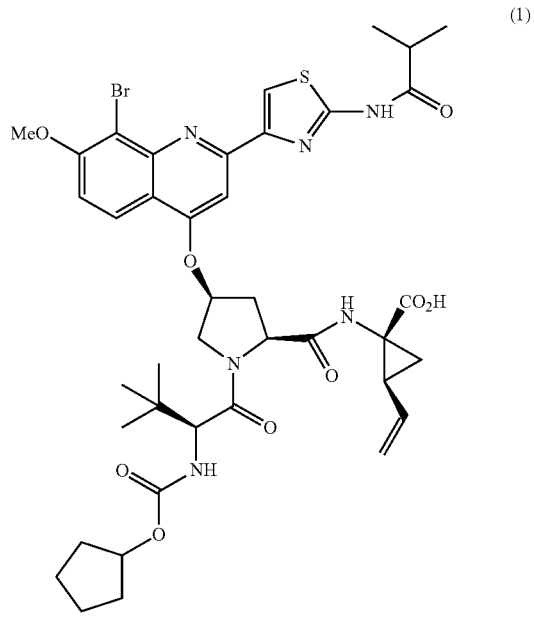 [SMILES: C=C[C@@H]1C[C@]1(NC(=O)[C@@H]1C[C@H](Oc2cc(-c3csc(NC(=O)C(C)C)n3)nc3c(Br)c(OC)ccc23)CN1C(=O)[C@@H](NC(=O)OC1CCCC1)C(C)(C)C)C(=O)O]

is known as a selective and potent inhibitor of the HCV NS3 serine protease and useful in the treatment of HCV infection. The bonding is significant for showing a particular stereochemistry of the compound. Compound (1) falls within the scope of the acyclic peptide series of HCV inhibitors disclosed in U.S. Pat. Nos. 6,323,180, 7,514,557 and 7,585,845. Compound (1) is disclosed specifically as Compound #1055 in U.S. Pat. No. 7,585,845, and as Compound #1008 in U.S. Pat. No. 7,514,557. Compound (1), and pharmaceutical formulations thereof, can be prepared according to the general procedures found in the above-cited references, all of which are herein incorporated by reference in their entirety. Preferred forms of Compound (1) include the crystalline forms, in particular the crystalline sodium salt form, which can be prepared as described in the examples section herein.

Compound (1) may also be known by the following alternate depiction of its chemical structure, which is equivalent to the above-described structure:

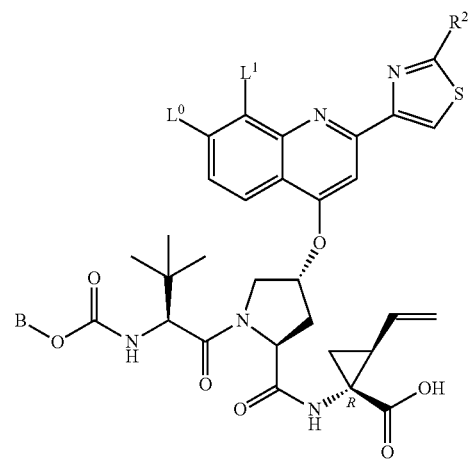

wherein B is

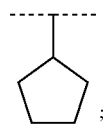

$L^0$ is MeO—; $L^1$ is Br; and $R^2$ is

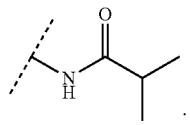

Although Compound (1) has been found generally effective in the reduction of viral load and the treatment of HCV infection, a certain amount of viral resistance with resulting viral rebound has been seen. For example, we have observed with Compound (1) given once-daily to treatment-naive patients as monotherapy for 14 days a strong and very rapid antiviral affect followed by a certain amount of resistance formation after 5-6 days.

Therefore, there is a continuing need in the field for alternative therapies for the treatment and prevention of HCV infection.

BRIEF SUMMARY OF THE INVENTION

The present invention provides a method of treating HCV infection or alleviating one or more symptoms thereof in a patient comprising the step of administering to the patient a therapeutic combination comprising a Compound (1) as defined herein, or a pharmaceutically acceptable salt thereof, together with an interferon alfa and ribavirin, as defined herein. The three actives of the combination can be administered simultaneously or separately, as part of a regimen. The references to Compound (1), interferon alfa and ribavirin below also refer to the use of the optional forms thereof defined below, e.g., salts and certain derivatives.

The present invention further provides methods for administering this therapeutic combination under defined regimens. In the discussion of the regimens below, all references to "Compound (1)" are intended to include all pharmaceutically acceptable salts thereof. A preferred form of Compound (1) in all regimens discussed herein is as the sodium salt.

In one regimen according to the invention, a lead-in therapeutic combination comprising the interferon alpha and the ribavirin, but not Compound (1), is administered for a defined period of time, and then the full therapeutic combination comprising the interferon alpha, the ribavirin and Compound (1) is administered. The lead-in time is preferably for the first 2 to 4 days of treatment, more preferably for the first 60 to 84 hours of treatment, and particularly for the first 3 days of treatment. By using this lead-in concept, one advantage is that this regimen should provide higher blood levels of interferon alpha and ribavirin at the beginning of the treatment. This is significant since high blood levels of interferon alpha and ribavirin seems to be important in suppressing the emergence of viral resistant strains at the beginning of the therapy.

In another regimen according to the invention, a loading dose amount of Compound (1) is administered for the first administration dose of the treatment. The loading dose amount is higher than the dose amount administered for subsequent administrations in the treatment. Preferably, the loading dose amount is about double in quantity, by weight, of the amount in subsequent administrations in the treatment. For example, in one embodiment, the first dose of Compound (1) administered at dosage of about 240 mg and subsequent doses of Compound (1) are administered at a dosage of about 120 mg. In another embodiment, the first dose of Compound (1) administered at a dosage of about 480 mg and subsequent doses of Compound (1) are administered at a dosage of about 240 mg. In another embodiment, the first dose of Compound (1) administered is at a dosage of about 960 mg and subsequent doses of Compound (1) are administered at a dosage of about 480 mg.

By using this loading dose concept, a clear advantage is that is it thereby possible to achieve steady state levels of active drug in the patient's system earlier than would otherwise be achieved. The blood level achieved by using a doubled loading dose is the same as would be achieved with a double dose but without the safety risk attendant to the subsequent continuous administration of a double dose. By reaching the targeted steady state level of active drug earlier in therapy also means that there less possibility of insufficient drug pressure at the beginning of therapy so that resistant viral strains have a smaller chance of emerging.

In another embodiment of the invention, the lead-in dosing regimen is combined with the loading dose regimen. Thus, a therapeutic combination comprising the interferon alpha and the ribavirin, but not Compound (1), is administered for a period of time followed by the full therapeutic combination comprising the interferon alpha, the ribavirin and Compound (1), as described above, and wherein for the first administration of Compound (1) a loading dose amount of Compound (1) is administered that is higher than the dose amount for Compound (1) administered for subsequent administrations in the treatment. The loading doses for this combined regimen may be as described above.

In another embodiment of the invention, a follow-up therapeutic combination comprising only the interferon alpha and the ribavirin, but not Compound (1), is administered for a period of time after the period of time when the full therapeutic combination comprising the interferon alpha, the ribavirin and Compound (1) is administered. In one embodiment of the follow-up regimen, the full therapeutic combination is administered for 24 weeks and the follow-up therapeutic combination is administered for a further 24 weeks. In another embodiment of the follow-up regimen, the full therapeutic combination is administered for 28 weeks and the follow-up therapeutic combination is administered for a further 20 weeks. Additional possibilities are as described hereinafter. The follow-up dosing regimen can be combined with the lead-in dosing regimen and/or the loading dose regimens described above.

The present invention further provides for a kit comprising a first pharmaceutical composition comprising a Compound (1); a second pharmaceutical composition comprising an interferon alfa; and a third pharmaceutical composition comprising ribavirin. The present invention further provides for such kits including instructions for administering the components of the therapeutic combination. In other embodiments of the invention, the kit includes instructions for administering which follow one or more of the above-described regimens for administering the therapeutic combination.

An additional embodiment is directed to a packaged pharmaceutical composition comprising a packaging containing multiple doses of Compound (1) or a pharmaceutically acceptable salt thereof and written instructions directing the co-administration of an interferon-alpha and ribavirin, and also directing that the first dose of Compound (1), or a pharmaceutically acceptable salt thereof, that is administered to the patient is double in quantity by weight to the subsequent doses thereof.

DETAILED DESCRIPTION OF THE INVENTION

Definitions

Figure 1:
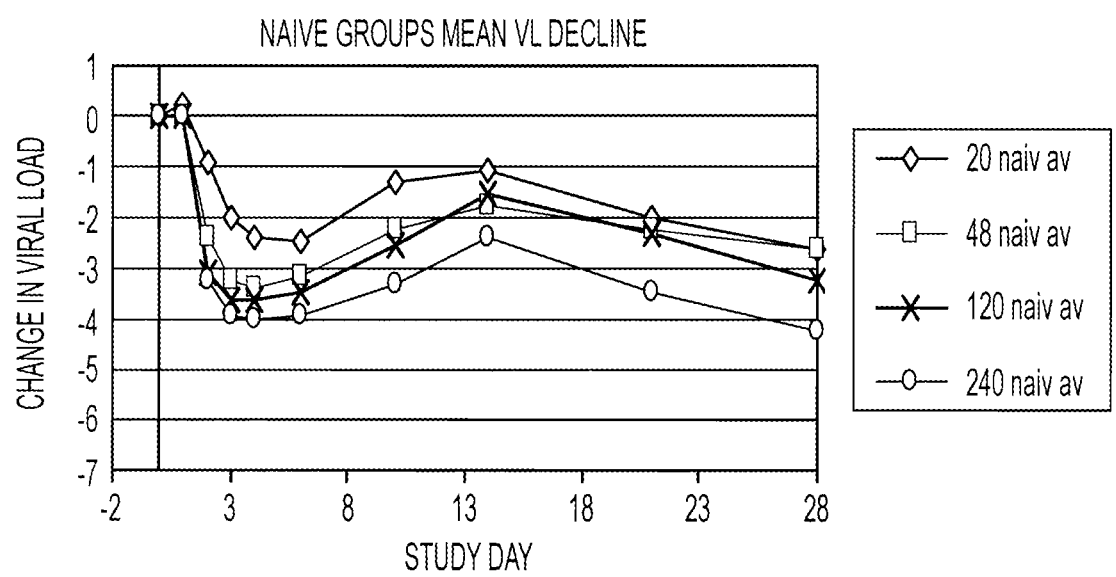
FIG. 1 depicts the average change in HCV viral load in four patient dose groups for treatment-naive patients with chronic HCV genotype-1 infection treated with Compound (1) sodium salt as monotherapy for 14 days, followed by combination therapy with Compound (1) sodium salt, pegylated interferon alfa-2a and ribavirin for an additional 14 days.

"Compound (1)" is as defined above.

"Interferon" means a member of a family of highly homologous species-specific proteins that inhibit viral replication and cellular proliferation and modulate immune response. Human interferons are grouped into three classes based on their cellular origin and antigenicity: α-interferon (leukocytes), β-interferon (fibroblasts) and γ-interferon (B cells). Recombinant forms of each group have been developed and are commercially available. Subtypes in each group are based on antigenic/structural characteristics. At least 24 interferon alfas (grouped into subtypes A through H) having distinct amino acid sequences have been identified by isolating and sequencing DNA encoding these peptides. The terms "α-interferon", "alfa-interferon" and "interferon alfa" are used interchangeably in this application to describe members of this group. Both naturally occurring and recombinant alfa-interferons, including consensus interferon, may be used in the practice of the invention.

Suitable interferon-alfas for the present invention include, but are not limited to, recombinant interferon alfa-2b such as INTRON®-A interferon and VIRAFERON®; recombinant interferon alfa-2a such as ROFERON® interferon; recombinant interferon alfa-2c such as BEROFOR® alfa 2 interferon; interferon alfa-n1, a purified blend of natural alfa interferons such as SUMIFERON® or WELLFERON® interferon alfa-n1 (INS); or a consensus alfa interferon such as those described in U.S. Pat. Nos. 4,897,471 and 4,695,623; or interferon alfa-n3, a mixture of natural alfa interferons such as ALFERON®. The use of interferon alfa-2a or alfa 2b is preferred. The manufacture of interferon alfa 2b is described in U.S. Pat. No. 4,530,901.

The term "interferon alfa" is further intended to include those "pegylated" analogs meaning polyethylene glycol modified conjugates of interferon alfa, preferably interferon alfa-2a and -2b. The preferred polyethylene-glycol-interferon alfa-2b conjugate is $PEG_{12000}$-interferon alfa 2b. The term "$PEG_{12000}$-IFN alfa" as used herein means conjugates such as are prepared according to the methods of International Application No. WO 95/13090 and containing urethane linkages between the interferon alfa-2a or -2b amino groups and polyethylene glycol having an average molecular weight of 12000.

The preferred $PEG_{12000}$-interferon alfa-2b is prepared by attaching a PEG polymer to the epsilon amino group of a lysine residue in the IFN alfa-2b molecule. A single $PEG_{12000}$ molecule is conjugated to free amino groups on an IFN alfa-2b molecule via a urethane linkage. This conjugate is characterized by the molecular weight of $PEG_{12000}$ attached. The $PEG_{12000}$-IFN alfa-2b conjugate is formulated as a lyophilized powder for injection. The objective of conjugation of IFN alfa with PEG is to improve the delivery of the protein by significantly prolonging its plasma half-life, and thereby provide protracted activity of IFN alfa.

Especially preferred conjugates of interferon alfa that may be used in the present invention are pegylated alfa-interferons, e.g., pegylated interferon alfa-2a, pegylated interferon alfa-2b, pegylated consensus interferon or pegylated purified interferon alfa product. Pegylated interferon alfa-2a is described, e.g., in European Patent No. EP 0 593 868 and commercially-available, e.g., under the tradename PEGA-SYS® (Hoffmann-La Roche). Pegylated interferon alfa-2b is described, e.g., in U.S. Pat. No. 5,908,621 and WO 98/48840 and commercially-available, e.g., under the tradename PEG-INTRON® A (Schering Plough). Pegylated consensus interferon is described in WO 96/11953. The preferred pegylated alfa interferons are pegylated interferon alfa-2a and pegylated interferon alfa-2b. Also preferred is pegylated consensus interferon.

The term "interferon alfa" further includes other interferon alfa conjugates that can be prepared by coupling an interferon alfa to a water-soluble polymer. A non-limiting list of such polymers includes other polyalkylene oxide homopolymers such as polyethylene glycol (PEG), polypropylene glycols, polyoxyethylenated polyols, copolymers thereof and block copolymers thereof. As an alternative to polyalkylene oxide-based polymers, effectively non-antigenic materials such as dextran, polyvinylpyrrolidones, polyacrylamides, polyvinyl alcohols, carbohydrate-based polymers and the like can be used. Such interferon alfa-polymer conjugates are described in U.S. Pat. No. 4,766,106, U.S. Pat. No. 4,917,888, European Patent Application No. 0 236 987, European Patent Application Nos. 0510 356, 0 593 868 and 0 809 996 (pegylated interferon alfa-2a) and International Publication No. WO 95/13090.

The term "interferon alfa" further includes fusion proteins of an interferon alfa, for example fusion proteins of interferon-α-2a, interferon-α-2b, consensus interferon or purified interferon-α product, each of which is fused with another protein. Certain preferred fusion proteins comprise an interferon (e.g., interferon-α-2b) and an albumin as described in U.S. Pat. No. 6,972,322 and international publications WO2005/003296 and WO2005/077042. A preferred interferon conjugated to a human albumin is ALBUFERON® which is a longer-acting form of interferon alfa created using albumin fusion technology. ALBUFERON® results from the genetic fusion of human albumin and interferon alpha. Also included are consensus interferons, such as INFERGEN®.

The term "pharmaceutically acceptable salt" means a salt of a Compound of formula (1) which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use.

The term includes pharmaceutically-acceptable acid addition salts and pharmaceutically-acceptable base addition salts. Exemplary lists of suitable salts are found in, e.g., S. M. Birge et al., *J. Pharm. Sci.,* 1977, 66, pp. 1-19.

The term "pharmaceutically-acceptable acid addition salt" means those salts which retain the biological effectiveness and properties of the free bases and which are not biologically or otherwise undesirable, formed with inorganic acids such as hydrochloric acid, hydrobromic acid, sulfuric acid, sulfamic acid, nitric acid, phosphoric acid, and the like, and organic acids such as acetic acid, trifluoroacetic acid, adipic acid, ascorbic acid, aspartic acid, benzenesulfonic acid, benzoic acid, butyric acid, camphoric acid, camphorsulfonic acid, cinnamic acid, citric acid, digluconic acid, ethanesulfonic acid, glutamic acid, glycolic acid, glycerophosphoric acid, hemisulfic acid, hexanoic acid, formic acid, fumaric acid, 2-hydroxyethane-sulfonic acid (isethionic acid), lactic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, pivalic acid, propionic acid, pyruvic acid, salicylic acid, stearic acid, succinic acid, sulfanilic acid, tartaric acid, p-toluenesulfonic acid, undecanoic acid, and the like.

The term "pharmaceutically-acceptable base addition salt" means those salts which retain the biological effectiveness and properties of the free acids and which are not biologically or otherwise undesirable, formed with inorganic bases such as ammonia or hydroxide, carbonate, or bicarbonate of ammonium or a metal cation such as sodium, potassium, lithium, calcium, magnesium, iron, zinc, copper, manganese, aluminum, and the like. Particularly preferred are the ammonium, potassium, sodium, calcium, and magnesium salts. Salts derived from pharmaceutically-accepta-ble organic nontoxic bases include salts of primary, secondary, and tertiary amines, quaternary amine compounds, substituted amines including naturally occurring substituted amines, cyclic amines and basic ion-exchange resins, such as methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, methylglucamine, theobromine, purines, piperazine, piperidine, N-ethylpiperidine, tetramethylammonium compounds, tetraethylammonium compounds, pyridine, N,N-dimethylaniline, N-methylpiperidine, N-methylmorpholine, dicyclohexylamine, dibenzylamine, N,N-dibenzylphenethylamine, 1-ephenamine, N,N'-dibenzylethylenediamine, polyamine resins, and the like. Particularly preferred organic nontoxic bases are isopropylamine, diethylamine, ethanolamine, trimethylamine, dicyclohexylamine, choline, and caffeine.

"Ribavirin" refers to 1-β-D-ribofuranosyl-1H-1,2,4-triazole-3-carboxamide, available from ICN Pharmaceuticals, Inc., Costa Mesa, Calif. and is described in the Merck Index, compound No. 8199, Eleventh Edition. Its manufacture and formulation is described in U.S. Pat. No. 4,211,771. Preferred marketed ribavirin products include REBETOL® and COPEGUS®. The term further includes derivatives or analogs thereof, such as those described in U.S. Pat. Nos. 6,063,772, 6,403,564 and 6,277,830. For example, derivatives or analogs include modified ribavirins such as 5'-amino esters, ICN Pharmaceutical's L-enantiomer of ribavirin (ICN 17261), 2'-deoxy derivatives of ribavirin and 3-carboxamidine derivatives of ribavirin, viramidine (previously known as ribamidine) and the like.

The term "therapeutic combination" as used herein means a combination of one or more active drug substances, i.e., compounds having a therapeutic utility. Typically, each such compound in the therapeutic combinations of the present invention will be present in a pharmaceutical composition comprising that compound and a pharmaceutically acceptable carrier. The compounds in a therapeutic combination of the present invention may be administered simultaneously or separately, as part of a regimen.

Embodiments of the Invention

According to a general embodiment, the present invention provides for a method of treating HCV infection or alleviating one or more symptoms thereof in a patient comprising administering to the patient a therapeutic combination comprising a Compound (1) as defined herein, or a pharmaceutically acceptable salt thereof, together with an interferon alfa and ribavirin according to one of the above-described regimens. In another embodiment, the present invention teaches the use of a Compound (1) as defined herein, or a pharmaceutically acceptable salt thereof, an interferon alfa, and ribavirin for the preparation of a pharmaceutical kit to treat a hepatitis C viral (HCV) infection or alleviating one or more symptoms thereof in a patient according to one of the above-described regimens.

Although this combination therapy is expected to be effective against all HCV genotypes, it has been demonstrated to be particularly effective in treating HCV genotype 1 infection, including subgenotypes 1a and 1b.

The patient population to be treated with the combination therapy of the present invention can be further classified into "treatment-naive" patients, i.e., those patient who have not received any prior treatment for HCV infection and "treatment experienced" patients, i.e., those patients who have undergone prior treatment for HCV. Either of these classes of patients may be treated with the combination therapy according to one of the above-described regimens of the present invention. A particular class of patients that are preferably treated are those treatment experienced patients that have undergone prior interferon plus ribavirin therapy but are non-responsive to said therapy (herein "non-responders"). Such non-responders include three distinct groups of patients: (1) those who experienced <1×$\log_{10}$ maximum reduction in HCV RNA levels during treatment with interferon plus ribavirin ("null responders"), (2) those who experienced ≥1×$\log_{10}$ maximum reduction in HCV RNA levels during treatment with interferon plus ribavirin but never achieve HCV RNA levels below level of detection ("partial responders"), and (3) those who achieved a virologic response with and during interferon plus ribavirin therapy but had a viral load rebound either during treatment (other than due to patient non-compliance) or after treatment has completed ("relapser"). As will be detailed below, particularly surprising results have been obtained with the treatment of certain non-responder patients using the combination therapy regimen of the present invention.

According to an alternative embodiment, the present invention provides a method of reducing HCV-RNA levels in a patient in need thereof, comprising the step of administering to said patient a therapeutic combination according to one of the above-described regimens of the present invention. Preferably, the method of the present invention reduces the HCV-RNA levels in a patient to a less than detectable level. The terms "less than detectable level" and "below level of detection" are used interchangeably herein and have the same meaning as being less than a detectable level of HCV RNA. A detectable level of HCV RNA as used in the present invention means at least 50 International Units (IU) per ml of serum of a patient as measured by quantitative, multi-cycle reverse transcriptase PCR methodology according to the WHO international standard (Saladanha J, Lelie N and Heath A, Establishment of the first international standard for nucleic acid amplification technology (NAT) assays for HCV RNA. WHO Collaborative Study Group. Vox Sang 76:149-158, 1999). Such methods are well known in the art. In a preferred embodiment, the method of the present invention reduces the HCV-RNA levels in a patient to less than 25 IU per ml of serum, even more preferably to less than 10 IU per ml of serum.

The usual duration of the treatment for standard interferon plus ribavirin therapy is at least 48 weeks for HCV genotype 1 infection, and at least 24 weeks for HCV genotypes 2 and 3. However, with the addition of Compound (1), or a pharmaceutically acceptable salt thereof, in the triple combination therapy of the present invention, it may be possible to have a much shorter duration of treatment. With the triple combination therapy of the present invention the contemplated durations of treatment include at least 4 weeks, preferably at least 12 weeks, e.g., from about 12 weeks to about 24 weeks, although treatment up to and even beyond 48 weeks is possible as well. Thus, further embodiments include treatment for at least 24 weeks and for at least 48 weeks. The time period for different HCV genotypes, e.g. HCV genotypes 2, 3 or 4 is expected to be similar. Also contemplated is an initial treatment regimen with the triple combination therapy of the present invention, followed by a continuation of only the interferon plus ribavirin double combination therapy. Thus, possible scenarios for the initial triple and then double combination therapy include, for example: (1) 4 weeks of the triple combination therapy, followed by 20 to 44 weeks of the interferon plus ribavirin only therapy; (2) 12 weeks of the triple combination therapy, followed by 12 to 36 weeks of the interferon plus ribavirin only therapy; and (3) 24 weeks of the triple combination therapy, followed by 12 to 24 weeks of the interferon plus ribavirin only therapy, any of which regimens may be used with any of the above-described treatment regimens including lead-in and/or loading dosing.

The first component of the therapeutic combination, namely, Compound (1) or a pharmaceutically acceptable salt thereof is comprised in a composition. Such a composition comprises Compound (1), or a pharmaceutically acceptable salt thereof, and a pharmaceutically acceptable adjuvant or carrier. Examples of pharmaceutical compositions that may be used for Compound (1), or a pharmaceutically acceptable salt thereof, are as described in U.S. Pat. No. 7,514,557.

In general, the Compound (1) or a pharmaceutically acceptable salt thereof may be administered at a dosage of at least 40 mg/day (in single or divided doses). Additional embodiments for dosage amounts and ranges may include (in single or divided doses):

(a) at least 48 mg/day
(b) at least 100 mg/day
(c) at least 120 mg/day
(d) at least 200 mg/day
(e) at least 240 mg/day
(f) at least 360 mg/day
(g) at least 480 mg/day
(h) from about 40 mg/day to about 480 mg/day
(i) from about 48 mg/day to about 240 mg/day
(j) from about 100 mg/day to about 300 mg/day
(k) from about 120 mg/day to about 300 mg/day
(l) from about 120 mg/day to about 240 mg/day
(m) from about 240 mg/day to about 480 mg/day
(n) about 48 mg/day
(o) about 120 mg/day
(p) about 240 mg/day
(q) about 360 mg/day
(r) about 480 mg/day Of course, the loading dose concept of the present invention may be used with any of the above-described dosage amounts or ranges (a) to (r) by increasing the amount of the initial dose of Compound (1), or a pharmaceutically acceptable salt thereof, administered. In one embodiment the initial dose is double the amount of the subsequent doses administered.

Although Compound (1) or a pharmaceutically acceptable salt thereof may be administered in single or divided daily doses, once a day administration of the daily dose is preferred. As the skilled artisan will appreciate, however, lower or higher doses than those recited above may be required. Specific dosage and treatment regimens for any particular patient will depend upon a variety of factors, including the age, body weight, general health status, sex, diet, time of administration, rate of excretion, drug combination, the severity and course of the infection, the patient's disposition to the infection and the judgment of the treating physician. In general, the compound is most desirably administered at a concentration level that will generally afford antivirally effective results without causing any harmful or deleterious side effects.

The second component of the therapeutic combination, namely an interferon-alfa, is comprised in a pharmaceutical composition. Typically, such compositions are injectible formulations comprising interferon-alfa and a pharmaceutically acceptable adjuvant or carrier and are well known in the art, including in a number of marketed interferon-alfa formulations. See, e.g., the various marketed interferon-alfa products and various patent and other literature related to interferon-alfa cited hereinabove.

The types of interferon-alfas that may be used in the combination are as outlined hereinabove in the definitions section. In one preferred embodiment, the interferon alfa is a pegylated interferon alfa. In a further embodiment, the interferon alfa is a pegylated interferon alfa-2a or pegylated interferon alfa-2b. In a particularly preferred embodiment, the interferon alfa is PEGASYS® or PEG-INTRON®.

When using known, marketed interferon alfa products, such products may be administered at their labeled dosage levels indicated for interferon plus ribavirin combination therapy for the treatment of HCV infection. Of course, with the triple combination therapy of the present invention it may be possible to use a lower dosage of interferon alfa, e.g., significantly lower than is used the current standard interferon plus ribavirin therapy, while delivering the same or better efficacy than the current standard therapy with less side-effects usually associated with such therapy.

In one embodiment, the interferon alfa may be administered parenterally one to three times per week, preferably once or twice a week. With respect to pegylated interferon alfas, these are typically administered once per week and the total weekly dose ranges, e.g., from about 0.5 µg/kg/week to about 2 µg/kg/week in case of pegylated interferon alfa-2b, and with respect to pegylated interferon alfa-2a the dosage is independent from the body weight of the host and is typically about 90 to 200 µg/week, more preferably about 160 to about 200 µg/week. In combination with ribavirin, a standard dosage of pegylated interferon alfa-2b is about 1.5 µg/kg/week and a standard dosage of pegylated interferon alfa-2a is about 180 μg/week, together with about 600-1200 mg/day, in particular, 800-1200 mg/day of oral ribavirin.

According to further embodiments, the pegylated interferon alfa-2b may be administered at dosages of:
- (a) about 0.5 μg/kg/week to about 2 μg/kg/week;
- (b) about 1 μg/kg/week to about 2 μg/kg/week;
- (c) about 1.5 μg/kg/week to about 2 μg/kg/week;
- (d) about 1.5 μg/kg/week According to further embodiments, the pegylated interferon alfa-2a may be administered at dosages of:
- (a) about 90 to about 200 μg/week;
- (b) about 160 to about 200 μg/week;
- (b) about 180 μg/week The third component of the therapeutic combination, namely ribavirin, is comprised in a pharmaceutical composition. Typically, such compositions comprise ribavirin and a pharmaceutically acceptable adjuvant or carrier and are well known in the art, including in a number of marketed ribavirin formulations. Formulations comprising ribavirin are also disclosed, e.g., in U.S. Pat. No. 4,211,771.

The types of ribavirin that may be used in the combination are as outlined hereinabove in the definitions section. In one preferred embodiment, the ribavirin is either REBETOL® or COPEGUS® and they may be administered at their labeled dosage levels indicated for interferon plus ribavirin combination therapy for the treatment of HCV infection. Of course, with the triple combination therapy of the present invention it may be possible to use a lower dosage of ribavirin, e.g., lower than is used the current standard interferon plus ribavirin therapy, while delivering the same or better efficacy than the current standard therapy with less side-effects usually associated with such therapy.

According to various embodiments, the ribavirin may be administered at dosages of (in single or divided doses):
- (a) between 400 mg/day to about 1200 mg/day;
- (b) between about 800 mg/day to about 1200 mg/day;
- (c) between about 1000 mg/day to about 1200 mg/day;
- (d) about 1000 mg/day
- (e) about 1200 mg/day
- (f) between about 300 mg/day to about 800 mg/day
- (g) between about 300 mg/day to about 700 mg/day
- (h) between 500 mg/day to about 700 mg/day
- (i) between 400 mg/day to about 600 mg/day
- (j) about 400 mg/day
- (k) about 600 mg/day
- (l) about 800 mg/day According to one embodiment, the ribavirin composition comprises ribavirin in a formulation suitable for dosing once a day, twice daily, thrice daily, four times a day, five times a day, or six times a day. For example, if a therapeutic combination comprises about 1000 mg/day dosage of ribavirin, and a dosing of five times a day is desired, then the therapeutic combination will comprise ribavirin in a formulation, e.g., a tablet, containing, e.g., about 200 mg of ribavirin.

With respect to the Compound (1) or a pharmaceutically acceptable salt thereof plus interferon alfa plus ribavirin triple combination therapy of the present invention, the present invention contemplates and includes all combinations of the various preferred embodiments and sub-embodiments as set forth hereinabove. Particularly preferred are the embodiments including the lead-in treatment regimen and/or the loading dose treatment regimen.

Examples of embodiments of the present invention include those having the lead-in and/or loading dose regimens described above in a method of treating hepatitis C viral (HCV) infection or alleviating one or more symptoms thereof in a patient wherein, after the lead-in and/or loading dose administration, the dosing of the three components is according to one of the following combinations (1) to (3):

(1)
- (a) Compound (1) or a pharmaceutically acceptable salt thereof at a dosage between about 48 mg per day and about 480 mg per day;
- (b) pegylated interferon alfa-2a at a dosage of about 160 to about 200 μg/week or pegylated interferon alfa-2b at a dosage of about 0.5 μg/kg/week to about 2 μg/kg/week; and
- (c) ribavirin at a dosage of between about 400 mg/day to about 1200 mg/day.

(2)
- (a) Compound (1) or a pharmaceutically acceptable salt thereof at a dosage between about 48 mg per day and about 480 mg per day;
- (b) pegylated interferon alfa-2a at a dosage of about 180 μg/week; and
- (c) ribavirin at a dosage of between about 1000 mg/day to about 1200 mg/day.

(3)
- (a) Compound (1) or a pharmaceutically acceptable salt thereof at a dosage between about 48 mg per day and about 480 mg per day;
- (b) pegylated interferon alfa-2b at a dosage of about 1.5 μg/kg/week; and
- (c) ribavirin at a dosage of about 800 mg/day.

In another embodiment of the loading dose regimen, Compound (1) or a pharmaceutically acceptable salt thereof is administered in a loading dose of 480 mg on day 1 and 240 mg/day on subsequent days, preferably by once daily administration (QD dosing), together with 180 μg/week of pegylated interferon alpha, preferably by weekly injection, and 1000-1200 mg/day of ribavirin, preferably by once daily administration. In an alternative of this loading dose regimen, the loading dose of Compound (1) or a pharmaceutically acceptable salt thereof is 480 mg in the first dose with subsequent doses of Compound (1) or a pharmaceutically acceptable salt thereof at 240 mg twice per day (BID dosing). In another alternative of the this loading dose regimen, the loading dose of Compound (1) or a to pharmaceutically acceptable salt thereof on day 1 is 240 mg and the subsequent daily doses of Compound (1) or a pharmaceutically acceptable salt thereof are 120 mg/day preferably by once daily administration.

In another alternative of these regimens, a lead in dosing period is included. Thus, for days 1-3 no Compound (1) or a pharmaceutically acceptable salt thereof is administered—only the pegylated interferon alpha and ribavirin are administered for the first 3 days. The above-described loading dose of Compound (1) or a pharmaceutically acceptable salt thereof is administered on day 4 and the treatment with the subsequent doses of Compound (1) or a pharmaceutically acceptable salt thereof together with the pegylated interferon alpha and ribavirin are continued as described for the balance of the first 24 weeks. In further embodiments, each of the above described alternative regimens is followed by a follow up treatment for 24 weeks of only the pegylated interferon alpha and ribavirin at the above-described doses without Compound (1) or a pharmaceutically acceptable salt thereof. In further alternative embodiments of each of the above described regimens, the treatment with the full combination of Compound (1) or a pharmaceutically acceptable salt thereof, the pegylated interferon alpha and ribavirin is for 28 weeks and follow up treatment with the pegylated interferon alpha and ribavirin at the above-described doses without Compound (1) or a pharmaceutically acceptable salt thereof is for 20 weeks.

Further embodiments include any of the above-mentioned embodiments, where:
(a) the HCV infection is genotype 1 and the patient is a treatment-naive patient; or
(b) the HCV infection is genotype 1 and the patient is a treatment-experienced patient who is non-responsive to a combination therapy of interferon plus ribavirin.

Further embodiments include any of the above-mentioned embodiments where the Compound (1) or a pharmaceutically acceptable salt thereof is administered once a day, the interferon alpha is administered once a week and the ribavirin is administered twice a day.

According to another embodiment, the therapeutic regimen of the present invention comprises administering the triple combination of Compound (1) or a pharmaceutically acceptable salt thereof, the interferon alfa and the ribavirin to a patient for at least about 4 weeks, more preferably either at least about 12 weeks or at least about 24 weeks.

According to another embodiment, the present invention provides kits for use in treating HCV infection in a patient. The kits of the present invention may comprise any of the therapeutic combinations of the present invention. The kits further comprise instructions for utilizing the therapeutic combinations to achieve any of the above-described treatment regimens. The kits may be tailored to the needs of classes or types of patients or other clinically relevant factors such as age, body weight, concomitant diseases/conditions, severity and stage of HCV infection, responsiveness or non-responsiveness to prior treatments, propensity for side effects, etc.

According to another embodiment, the present invention provides a kit comprising:
(a) a first pharmaceutical composition comprising a Compound (1) or a pharmaceutically acceptable salt thereof:
(b) a second pharmaceutical composition comprising interferon alfa;
(c) a third pharmaceutical composition comprising ribavirin; and.
(d) instructions for utilizing the above compositions to achieve any of the above-described treatment regimens.

An additional embodiment is directed to a packaged pharmaceutical composition comprising a packaging containing multiple doses of Compound (1) or a pharmaceutically acceptable salt thereof and written instructions directing the co-administration of an interferon-alpha and ribavirin, and also directing that the first dose of Compound (1), or a pharmaceutically acceptable salt thereof, that is administered to the patient is double in quantity by weight to the subsequent doses thereof. The individual doses of Compound (1) or a pharmaceutically acceptable salt thereof can be in the form of any of the standard pharmaceutical dosage forms, e.g. tablets, capsules, and packaged within any of the standard types of pharmaceutical packaging materials, e.g. bottles, blister-packs, etc., that may themselves be contained within an outer packaging material such as a paper/cardboard box. The written instructions will typically be provided either on the packaging material(s) itself or on a separate paper (a so-called "package insert") that is provided together with the dosage forms within the outer packaging material. All such packaging embodiments and variations thereof are embraced by the present invention.

Additionally, surprising results have been seen in the suppression of HCV viral resistance during the combination therapy treatment contemplated by the present invention. Dosing of Compound (1) (sodium salt) as a monotherapy resulted in a rapid viral load rebound in the first 14 days during treatment in a majority of the patients from all dose groups of treatment-naïve patients in whom viral load reductions were observed. In contrast, among the 19 treatment experienced patients who received Compound (1) (sodium salt) once daily (qd) doses of 48 mg (n=6), 120 mg (n=7), or 240 mg (n=6) in a combination with pegylated interferon alfa 2a and ribavirin (PegIFN/RBV) for 28 days, virologic rebound during the 28 day treatment was only observed in 2/6 patients in the 48 mg dose group, and in 1/7 patients in the 120 mg dose group. Notably, no rebound was seen during the first 28 days in the treatment-experienced dose group that received Compound (1) (sodium salt) 240 mg qd treatment in combination with PegIFN/RBV.

Accordingly, in an additional embodiment, there is limited or no emergence of viral resistance during the combination therapy of the present invention. In a more specific embodiment, there is limited or no emergence of HCV variants that encode HCV NS3 protease amino acid substitutions at one or more of R155 and/or D168 and/or A156 during the combination therapy of the present invention.

Further embodiments include any of the above-mentioned embodiments, and where either:
(a) the HCV infection is genotype 1a and the patient is a treatment-naive patient; or
(b) the HCV infection is genotype 1a and the patient is a treatment-experienced patient who is non-responsive to a combination therapy of interferon plus ribavirin;
and wherein there is limited or no emergence of variants that encode substitutions at NS3 protease amino acid R155 during the combination therapy of the present invention.

Further embodiments include any of the above-mentioned embodiments, and where either:
(a) the HCV infection is genotype 1b and the patient is a treatment-naive patient; or
(b) the HCV infection is genotype 1b and the patient is a treatment-experienced patient who is non-responsive to a combination therapy of interferon plus ribavirin;
and wherein there is limited or no emergence of the variants that encode substitutions at NS3 protease amino acid D168 during the combination therapy of the present invention.

EXAMPLES

I. Methods for Preparing Compound (1)

Methods for preparing amorphous Compound (1) can be found in U.S. Pat. Nos. 6,323,180, 7,514,557 and 7,585,845, which are herein incorporated by reference. The following Examples 1 to 5 provide methods for preparing additional forms of Compound (1) that may be used in the present invention.

Example 1

Preparation of Type A Crystalline Form of Compound (1)

Amorphous Compound (1) (Batch 7, 13.80 g) was added to a 1000 ml three neck flask. Absolute ethanol (248.9 g) was added to the flask. While stirring, the contents of the flask were heated at 60 degrees C./hr to ~74 degrees C. (Solids do not dissolve at 74 degrees C.). Water (257.4 g) was then added linearly over 4 hr to the resulting slurry while stirring and maintaining the temperature at 74 degrees C. After the water addition was complete, the temperature was reduced linearly to ambient temperature at 8 degrees C./hr and then held at ambient temperature for 6 hrs while stirring. The resulting solids were collected by filtration and washed with 50 ml of 1/1 (w/w) EtOH/Water. The wet solids were dried on the funnel for 30 minutes by sucking $N_2$ through the cake. (XRPD analysis on this sample indicates that the pattern is similar to the EtOH solvate). The solids were then dried at 65-70 degrees C. under vacuum (P=25 in Hg) and a nitrogen bleed for 1.5 hr. The resulting solids (12.6 g, 95.5% corrected yield) were confirmed by XRPD as being Type A Compound (1).

Example 2

Preparation of the Sodium Salt of Compound (1)—Method 1

2.1 g of amorphous sodium salt of Compound (1) and 8.90 g of acetone was added to a vial and stirred at ambient temperature for 3 hr. The slurry was filtered off mother liquors and the resulting solids were dried for 20 minutes under nitrogen flow for 20 minutes. 1.51 g of crystalline sodium salt of Compound (1) as solids was collected.

Example 3

Preparation of the Sodium Salt of Compound (1)—Method 2

15.6 g of Type A of Compound (1), 175 ml of acetone and 3.6 ml of water was added to a 250 ml reactor and heated to 53 degrees C. to dissolve the solids. 900 ul of 10.0 N NaOH was added to reactor and the solution was seeded with Type A. The seeded solution was stirred at 53 degrees C. for 10 minutes. A second 900 ul portion of 10.0; N NaOH was added and the system was stirred at 53 degrees C. for 30 minutes over which a slurry developed. The slurry was cooled to 19 degrees C. at a cooling rate of 15 degrees C. per hour and held overnight at 19 degrees C. The final resulting slurry was filtered and the wet solids were washed with 15 ml of acetone. Dried solids for 1 hr at 52 degrees C. under vacuum with a nitrogen flow and then exposed the solids to lab air for one hour. Collected 12.1 g of Compound (1) crystalline sodium salt solids.

Example 4

Preparation of the Sodium Salt of Compound (1)—Method 3

25.4 Kg of amorphous Compound (1), 228 L of THF and 11.1 Kg of 10 wt % NaOH (aq) was added to a reactor. The components were mixed at 25 degrees C. to dissolve all solids. The resulting solution was filtered and the reactor and filter was washed with 23 L of THF. 180 L of solvent was removed using atmospheric distillation at 65 degrees C. 195 L of MIBK was added and 166 L of solvent was removed by vacuum distillation at ~44 degrees C. 161 L of MIBK and 0.41 Kg of water was added back to the reactor and the contents were heated to 70 degrees C. 255 g of Compound (1) sodium salt seeds were added at 70 degrees C. and 1.42 L of water was added over 1.5 hours. After the water addition the slurry was held at 70 degrees C. for 45 minutes and then cooled to 45 degrees C. over 1 hr. The resulting slurried was filtered and washed with 64 L of MIBK containing ~0.8 weight % water. The wet cake was dried at 55 degrees C. to give ~25 Kg of crystalline sodium salt of Compound (1).

Example 5

Preparation of the Sodium Salt of Compound (1)—Method 4

2.00 g of amorphous Compound (1), 9.96 g of THF and 0.11 g of water was added to a reactor and stirred at ambient temperature to dissolve solids. 0.820 ml of 21 weight % NaOET in ethanol was added drop-wise while stirring the solution to get solution A. 15.9 g of n-BuAc and 160 ul of water was added to a second reactor and heated to 65 degrees C. (solution B). 2.56 g of Solution A was added to Solution B at 65 degrees C. and the resulting mixture was seeded with 40 mg of Compound (1) sodium salt seeds. The seeded mixture was aged at 65 degrees C. for 45 minutes. 2.56 g of Solution B was added to Solution A and aged for 45 minutes in four separate intervals. After the final addition and aging, the slurry was cooled to 50 degrees C. over 1 hour and filtered. The wet cake was washed with 6 ml of n-BuAc containing 0.5 weight % water. The final solids were dried at 50 degrees C. under vacuum using a nitrogen purge. Compound (1) crystalline sodium salt solids were collected.

II. Clinical Results

For the clinical trials described below, the drug product administered was an oral solution of Compound (1) sodium salt. The Compound (1) sodium salt was provided to the clinical site(s) as a powder for preparing an oral solution using a co-supplied solvent. The solvent was also used as the placebo.

Example 6

Clinical Study with Treatment-Naïve Patients

Safety and antiviral activity of Compound (1) sodium salt, a new HCV NS3 protease inhibitor, in treatment-naive patients with chronic hepatitis C genotype-1 infection given as monotherapy and in combination with Peginterferon alfa 2a (P) and Ribavirin (R)

Background: Compound (1) sodium salt is a HCV NS3 protease inhibitor ($EC_{50}$ of 3-6 nM). A multiple rising dose study evaluated safety and antiviral activity in treatment-naive patients (pts) with chronic HCV genotype-1 infection as monotherapy for 14 days followed by triple combination therapy with P+R for an additional 14 days.

Methods: 34 patients (France, Germany, Spain, USA) with a Metavir fibrosis score of 0-3 and no prior therapy with any interferon or R were randomized (2 placebo:6 or 7active) to 4 dose groups of once-daily (qd) Compound (1) sodium salt: 20 mg (n=8), 48 mg (n=9), 120 mg (n=9), or 240 mg (n=8). Compound (1) sodium salt was given as monotherapy for 14 days. Pts with <1 log 10 decrease in Day 10 viral load (VL) had Compound (1) sodium salt discontinued after Day 14. Pts with a ≥1 log 10 decrease in Day 10 VL continued Compound (1) sodium salt on Day 15 and added P(180 µg/week)+R (weight based) for triple combination therapy through Day 28. The primary endpoint was ≥2 log 10 VL reduction at any time to Day 14. Plasma HCV-RNA levels were measured with Roche COBAS® TaqMan® assay (LLOQ 25 IU/m L). After Day 28, at the discretion of the investigator, patients could continue to receive standard of care treatment, i.e., P+R.

Results: 33 pts were white, 1 was Asian, 27 were male, mean age=48.9±11.1 years, mean body weight 79.1±17.5 kg, and median (range) baseline VL was 6.8 (4.7-7.7) log 10. There were no significant demographic differences between dose groups. Compound (1) sodium salt was well tolerated. No pts discontinued treatment during monotherapy due to adverse events (AEs). AEs observed were typical for P+R. One serious AE, asthenia, occurred in the 20 mg dose cohort 6 days after initiating P+R. Rapid decline of VL was observed in all pts with maximal decline typically 2-4 days after starting Compound (1) sodium salt. With to the exception of 1 pt in the 20 mg cohort, all pts on Compound (1) sodium salt achieved >2 log 10 VL decline during the monotherapy period. Median (range) maximal reductions in VL during 14 day monotherapy for the 20 mg, 48 mg, 120 mg, and 240 mg groups were 3.0 (1.5-3.9), 3.6 (3.1-3.8), 3.7 (3.3-4.1), and 4.2 (3.6-4.8) log 10 IU/ml, respectively. No significant change in VL was observed with placebo. VL rebound during treatment was seen in the first 14 days of monotherapy in a majority of patients from all dose groups.

Conclusion: Compound (1) sodium salt as monotherapy for 14 days followed by combination with P+R for additional 14 days was well tolerated, and induced a strong and rapid antiviral response among treatment naïve patients.

FIG. 1 depicts the average change in HCV viral load in the four patient dose groups of this study, i.e., treatment-naïve patients with chronic HCV genotype-1 infection treated with Compound (1) sodium salt as monotherapy for 14 days, followed by combination therapy with Compound (1) sodium salt, pegylated interferon alfa-2a and ribavirin for an additional 14 days. In the figure, the change in viral load is in IU/ml log 10 units and the four patient dose groups are labeled as follows:

"20 naiv av"=average viral load change for 20 mg dose group
"48 naiv av"=average viral load change for 48 mg dose group
"120 naiv av"=average viral load change for 120 mg dose group
"240 naiv av"=average viral load change for 240 mg dose group Emergence of Variants During Treatment-Naïve Patient Therapy Population sequencing of the NS3/4A protease at baseline and rebound during treatment revealed selection of variants that confer in vitro resistance to Compound (1) sodium salt. There were seen notable changes at key residues within the NS3 protease domain relative to subtype reference (sub-genotype 1a: AF009606 or sub-genotype1b: AJ238799) during therapy in various dose groups. See Tables 1 to 4 below for details. In all tables, Gt represents the HCV subgenotype and Day 1 represents baseline sequence and the indicated amino acid substitutions are naturally occurring NS3 polymorphisms at key residues. Additional changes, that may encode or be associated with drug-resistance, are noted at different days during treatment.

TABLE 1

Predominant variants (relative to subtype reference) at key residues in the population-based amino acid sequences from the treatment-naïve patients in the 20 mg dose group

| Patient | Gt | Day of treatment | | | | | |
|---------|----|----|---|---|---|---|---|
| | | 1 | 6 | 14 | 28 | 56 | 168 |
| 20N1 | 1b | I71V, Q86P | I71V, Q86P | I71V, Q86P | ND | ND | ND |
| 20N2 | 1b | none | BLD | D168V | R155[K, Q, R], D168[D, V] | R155[K, Q, R], D168[D, V] | BLD |
| 20N3* | 1b | Q86A, V/I170T | Q86A, V/I170T | Q86A, V/I170T | BLD | BLD | BLD |
| 20N4 | 1a | none | V/I170[I, T] | R155K | R155K | R155K | BLD |
| 20N5 | 1b | Q80L, | Q80L, D168[G, A] | Q80L, D168[E, D] | BLD | BLD | BLD |
| 20N6 | 1a | none | none | none | ND | ND | ND |
| 20N7 | 1a | none | R155K | R155K | R155K | R155K | R155K |
| 20N8 | 1a | none | R155[R, K] | R155K | R155K | R155K | BLD |

None: no substitutions at the selected positions were observed
BLD: Below limit of detection for PCR amplification
ND: Not determined
*Encodes V/I170T baseline polymorphism.

TABLE 2

Predominant variants (relative to subtype reference) at key residues in the population-based amino acid sequences from the treatment-naïve patients in the 48 mg dose group.

| Patient | Gt | Day of treatment | | |
|---------|----|----|---|---|
| | | 1 | 14 | 28 |
| 48N1 | 1a | T54[T, S] | T54[T, S] | ND |
| 48N2 | 1b | I71V, Q86P | I71V, Q86P V170[E, V] | ND |
| 48N3 | 1b | P89S | P89S, D168V | P89S, D168V |
| 48N4 | 1b | I71V | I71V, D168V | T54[T, A], I71V, D168V |
| 48N5 | 1a | none | R155K | R155K |
| 48N6 | 1b | none | D168[T, I, A, V] | D168[T, I, A, V] |
| 48N7 | 1b | none | BLD | BLD |
| 48N8 | 1a | Q80K | Q80K, R155K | BLD |
| 48N9 | 1b | I71V, Q80[Q, R] | I71V, Q80[Q, R] R155[R, W], D168[D, V] | ND |

None: no substitutions at the selected positions were observed
BLD: Below limit of detection for sequencing
ND: Not determined

TABLE 3

Predominant variants (relative to subtype reference) at key residues in the population-based amino acid sequences from the treatment-naïve patients in the 120 mg dose group

| Patient | Gt | Day of treatment | | | |
|---------|----|----|---|---|---|
| | | 1 | 14 | 28 | 84 |
| 120N1 | 1a | Q80K | Q80K | ND | ND |
| 120N2 | 1 | D168D/E | D168D/E | ND | ND |
| 120N3 | 1a | none | R155K | BLD | BLD |
| 120N4 | 1a | Q80K | BLD | ND | ND |
| 120N5 | 1b | none | D168V | BLD | BLD |

TABLE 3-continued

Predominant variants (relative to subtype reference) at key residues in the population-based amino acid sequences from the treatment-naïve patients in the 120 mg dose group

| Patient | Gt | Day of treatment | | | |
|---|---|---|---|---|---|
| | | 1 | 14 | 28 | 84 |
| 120N6 | 1b | P89T | P89T, D168V | P89T, D168V | P89T, D168V |
| 120N7 | 1a | none | R155K | BLD | BLD |
| 120N8 | 1b | none | D168V | D168V | BLD |
| 120N9 | 1b | Q86P | Q86P, A156[T, A], D168[D, V] | Q86P, D168[D, I, A, V] | Q86P, R155K |

None: no substitutions at the selected positions were observed
BLD: Below limit of detection for sequencing
ND: Not determined

TABLE 4

Predominant variants (relative to subtype reference) at key residues in the population-based amino acid sequences from the treatment-naïve patients in the 240 mg dose group

| Patient | Gt | Day of Treatment | | | |
|---|---|---|---|---|---|
| | | 1 | 14 | 28 | 84 |
| 240N1 | 1b | Q80L, Q86P | Q80L, Q86P | ND | ND |
| 240N2 | 1b | none | none | ND | ND |
| 240N3 | 1a | V36[L, V], Q80K | V36L, Q80K, R155K | ND | V36L, Q80K, R155K |
| 240N4 | 1b | none | BLD | BLD | BLD |
| 240N5 | 1b | P89A | P89A, D168V | P89A, D168V | BLD |
| 240N6 | 1 | none | D168V | D168V | BLD |
| 240N7 | 1b | none | D168V | BLD | BLD |
| 240N8 | 1a | Q89P | BLD | BLD | BLD |

None: no substitutions at the selected positions were observed
BLD: Below limit of detection for PCR amplification and sequencing
ND: Not determined

Example 7

Clinical Study with Treatment-Experienced Patients

Safety and antiviral activity of Compound (1) sodium salt, a new HCV NS3 protease inhibitor, in combination therapy with Peginterferon alfa 2a (P) and Ribavirin (R) for 28 days in P+R treatment-experienced patients with chronic hepatitis C genotype-1 infection.

Background: Compound (1) sodium salt is a HCV NS3 protease inhibitor ($EC_{50}$ of 3-6 nM). A multiple rising dose study evaluated the safety and antiviral activity in P+R treatment-experienced patients (pts) with chronic hepatitis C genotype-1 infection for 28 days as combination therapy with P+R.

Methods: 19 pts (France, Germany, Spain, USA) with a Metavir fibrosis score of 0-3, who experienced previous virologic failure with P+R combination therapy, were assigned to receive Compound (1) sodium salt once-daily (qd) doses of 48 mg (n=6), 120 mg (n=7), or 240 mg (n=6) in combination with P (180 μg/wk)+R (weight based) for 28 days. All patients were monitored for safety and tolerability of study drugs. The primary endpoint was a ≥2 log 10 reduction in HCV viral load (VL) from baseline at any time up to Day 28. Plasma HCV-RNA levels were measured using the Roche COBAS® TaqMan® assay (LLOQ 25 IU/mL). The treatment experienced patients in this study included P+R null responders and partial respoders. After Day 28, at the discretion of the investigator, patients could continue to receive standard of care treatment, i.e., P+R.

Results: 19 pts were white, 11 were male, mean age was 48±9 years, mean body weight was 81±15 kg, and median (range) baseline VL was 6.9 (5.9-7.4) log 10. There were no significant demographic differences between dose groups. Compound (1) sodium salt was well tolerated and no serious or severe adverse events (AEs) were observed among pts in this study. AEs were typical for P+R. One subject discontinued treatment due to an AE (anxiety). A rapid, dose-related decline of VL was observed in all pts. All pts treated with Compound (1) sodium salt+P+R achieved >2 log 10 VL decline with triple combination therapy. Median (range) maximal decline in VL during 28 day combination therapy for 48 mg, 120 mg, and 240 mg dose cohorts was 4.8 (3.4-5.9), 5.2 (3.9-6.0), and 5.3 (4.8-6.1) log 10 IU/ml, respectively. Virologic rebound during treatment was observed during the first 28 days of Compound (1) sodium salt+P+R dosing in 2/6 pts in the 48 mg and in 1/7 pts in the 120 mg dose groups. In these patients, population sequencing of the NS3/4A protease at baseline and at viral rebound during treatment revealed selection of variants in the NS3 protease domain shown to confer in vitro resistance to Compound (1) sodium salt. One patient in the 120 mg dose group did not display virologic rebound, but plateaued with ~500 copies IU/ml VL by Day 28 and encoded a R155K mutant; this viral load sample was below the lower limit of detection in our phenotypic resistance assays.

No rebound during the 28-day Compound (1) treatment was seen in the 240 mg qd dose cohort: 5/6 pts had VL.<25 IU/mL at Day 28. The sixth pt had a 4.7 log 10 decline in VL from baseline on Day 28 and VL was <25 IU/ml at next visit, Day 42.

Conclusion: Compound (1) sodium salt given once-daily in combination therapy with P+R for 28 days was well tolerated, and induced a strong and rapid antiviral response among treatment experienced patients.

Figure 2:
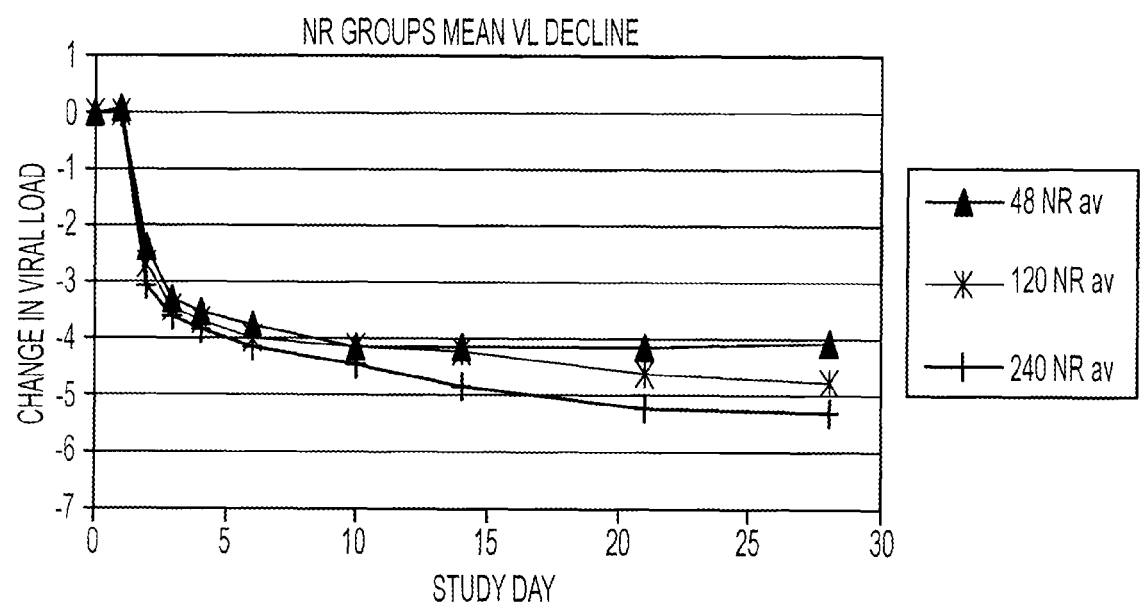
FIG. 2 depicts the average change in HCV viral load in three patient dose groups for treatment-experienced patients with chronic HCV genotype-1 infection treated with Compound (1) sodium salt, pegylated interferon alfa-2a and ribavirin as combination therapy for 28 days.

FIG. 2 depicts the average change in HCV viral load in three patient dose groups for this study, i.e., treatment-experienced patients with chronic HCV genotype-1 infection treated with Compound (1) sodium salt, pegylated interferon alfa-2a and ribavirin as combination therapy for 28 days. In the figure, the change in viral load is in IU/ml log 10 units and the four patient dose groups are labeled as follows:

"48 NR av"=average viral load change for 48 mg dose group

"120 NR av"=average viral load change for 120 mg dose group

"240 NR av"=average viral load change for 240 mg dose group

Certain parameters relating to the virologic response (reduction in viral load) in the patients in this study are shown in the following table (where "D"=day, and "QD"=once per day; "N"=# of patients; "Below Limit of Quantification" means less than 25 IU per ml of serum).

| 1220.2 Virologic Response in Treatment-experienced Patients | | | |
|---|---|---|---|
| | 48 mg QD N = 6 | 120 mg QD N = 7 | 240 mg QD N = 6 |
| Maximal decline D 1-14 ($\times\log_{10}$) | 4.4 (3.4-4.9) | 4.5 (3.6-5.2) | 4.8 (4.2-5.1) |
| Mean decline at D 6 ($\times\log_{10}$) | 3.8 | 4.0 | 4.2 |

-continued 1220.2 Virologic Response in Treatment-experienced Patients

|  | 48 mg QD N = 6 | 120 mg QD N = 7 | 240 mg QD N = 6 |
|---|---|---|---|
| Mean Decline at D 14 (×log$_{10}$) | 4.1 | 4.3 | 4.8 |
| Below Limit of Quantification at D 28 | 3 (50%) | 4 (57%) | 5 (83%) |

Emergence of Variants During Treatment-Experienced Patient Therapy

There are notable changes at key residues within the NS3 protease domain relative to subtype reference (sub-genotype 1a: AF009606 or sub-genotype 1b: AJ238799) during to therapy in various dose groups. See Tables 1 to 4 below for details. In all tables, Gt represents the HCV subgenotype and Day 1 represents baseline sequence and the indicated amino acid substitutions are naturally occurring NS3 polymorphisms at key residues. Additional changes, that may encode or be associated with drug-resistance, are noted at different days during treatment.

TABLE 5

Predominant variants (relative to subtype reference) at key residues in the population-based amino acid sequences from the 48 mg treatment-experienced dose group.

| Patient | Gt | Day of treatment | | | |
|---|---|---|---|---|---|
|  |  | 1 | 14 | 28 | 168 |
| 48TE1 | 1a | Q80K | Q80K | Q80K, R155K | Q80K, R155K |
| 48TE2 | 1a | Q80L | BLD | BLD | BLD |
| 48TE4 | 1a | Q80R | BLD | BLD | BLD |
| 48TE3 | 1b | none | D168V | D168V | R155R/K/Q |
| 48TE5 | 1b | Q86P | BLD | BLD | BLD |
| 48TE6 | 1b | Q86P | BLD | BLD | Q86P, R155K |

None: no substitutions at the selected positions were observed
BLD: Below limit of detection for PCR amplification and sequencing

TABLE 6

Predominant variants (relative to subtype reference) at key residues in the population-based amino acid sequences from the 120 mg treatment-experienced dose group.

| Patient | Gt | Day of Treatment | | |
|---|---|---|---|---|
|  |  | 1 | 14 | 28 |
| 120TE1 | 1a | Q80K | Q80K, R155K | Q80K, R155K |
| 120TE2 | 1a | Q89Y | BLD | BLD |
| 120TE3 | 1b | Q86P, P89S | BLD | BLD |
| 120TE4 | 1b | Q86A | BLD | BLD |
| 120TE5 | 1b | P89[P, S] | BLD | BLD |
| 120TE6 | 1a | none | BLD | BLD |
| 120TE7 | 1a | none | R155K* | R155K* |

None: no substitutions at the selected positions were observed
BLD: Below limit of detection for PCR amplification and sequencing
*VL plateau at <1000 IU/ml at these time points.

TABLE 7

Predominant variants (relative to subtype reference) at key residues in the population-based amino acid sequences from the 240 mg treatment-experienced dose group.

| Patient | Gt | Day of Treatment | |
|---|---|---|---|
|  |  | 1 | 28 |
| 240TE1 | 1a | none | BLD |
| 240TE2 | 1a | none | BLD |
| 240TE3 | 1a | none | BLD |
| 240TE4 | 1b | none | BLD |
| 240TE5 | 1b | Q86P | BLD |
| 240TE6 | 1a | none | BLD |

None: no substitutions at the selected positions were observed
BLD: Below limit of detection for PCR amplification and sequencing Example 8

Effect of a Two-Fold First Loading Dose on Achieving Higher Percent of Steady State Plateau Trough Concentration Background: Compound (1) sodium salt is a HCV NS3 protease inhibitor ($EC_{50}$ of 3-6 to nM). A study evaluated the effect of a two-fold first loading dose on the mean plasma concentrations of Compound (1) in P+R treatment-experienced patients with chronic hepatitis C genotype-1 infection when treated for 28 days as combination therapy with P+R.

Methods: Treatment experienced (TE) patients as describe in Example 7 (France, Germany, Spain, USA) received Compound (1) sodium salt once-daily (qd) doses of 240 mg without a 480 mg loading dose (n=6; received Compound (1) Na salt via an oral solution) or with a 480 mg loading dose (n=15; received Compound (1) Na salt via soft gelatin capsule) in combination with P (180 μg/wk)+R (weight based) for 28 days. Trough (pre-dose) plasma samples were collected on Days 2, 3, 4, 6, 10, 14, 21, 28 and 29 following the initiation of combination treatment on Day 1. Plasma concentrations of the active Compound (1) in these trough samples were determined by validated high performance liquid chromatography (HPLC)-tandem mass spectrometry) methods.

Figure 3:
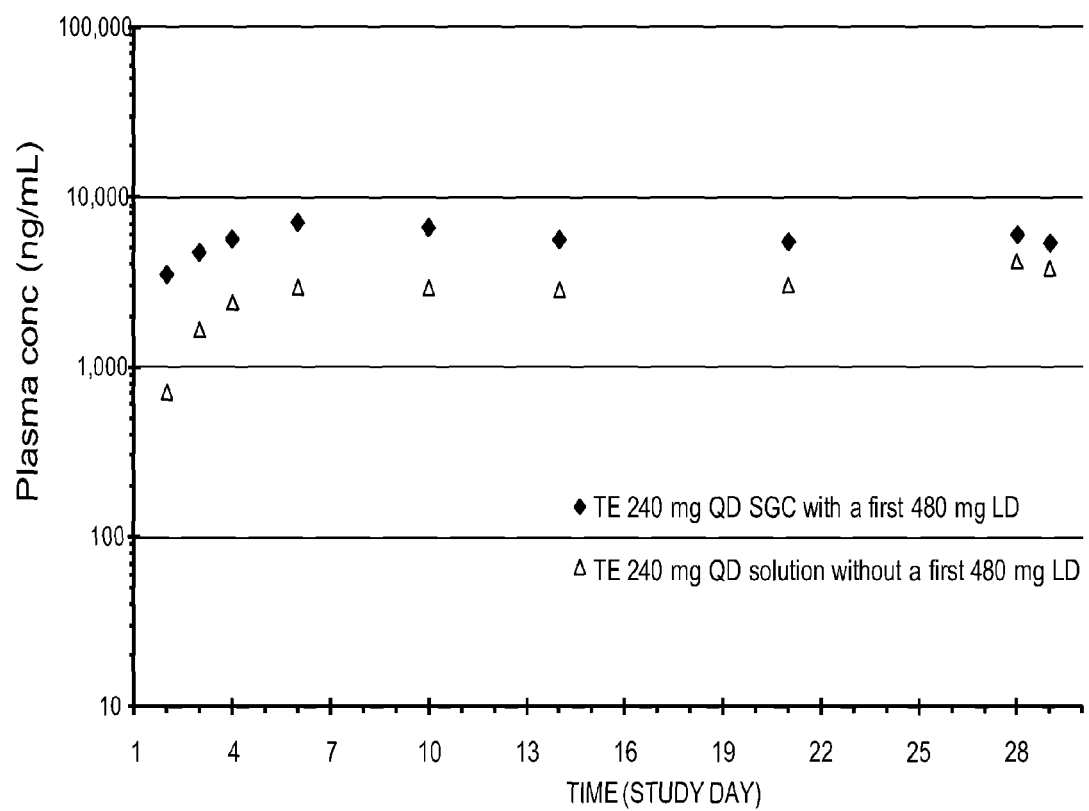
FIG. 3 depicts the geometric mean trough plasma concentration of Compound (1) in two patient groups for treatment-experienced patients with chronic HCV genotype-1 infection treated with Compound (1) sodium salt, pegylated interferon alfa-2a and ribavirin as combination therapy for 28 days, one patient group receiving a two-fold first loading dose of Compound (1) sodium salt and the other patient group not receiving such loading dose.

Results: Geometric trough plasma concentration of Compound (1) at different days during the study for the two treatment groups are summarized in Table 8 and depicted in FIG. 3. In Table 8, the plateau steady state trough concentrations were obtained by averaging the values from Days 10 to 29. The percentage of steady state trough concentrations on Days 2 to 6 are higher in the treatment group with a 2-fold first loading dose than the treatment group without a loading dose, although the mean steady state trough concentrations differ between the 2 treatment groups. FIG. 3 depicts the geometric mean trough plasma concentration of Compound (1) in the two 240 mg q.d. TE treatment groups for this study, i.e., with and without a 480 mg first loading dose.

TABLE 8

Effect of a 2-fold first loading dose on achieving higher percent of steady state plateau trough concentrations in the two 240 mg treatment-experienced dose groups

| Time (Day) | 240 mg QD soft gelatin capsules (SGC) with a first 480 mg loading dose in TE patients | 240 mg QD solution (PiB) without a first 480 mg loading dose in TE patients |
|---|---|---|
| 2 | 3,470 | 710 |
| 3 | 4,690 | 1,660 |

TABLE 8-continued

Effect of a 2-fold first loading dose on achieving higher percent of steady state plateau trough concentrations in the two 240 mg treatment-experienced dose groups

| Time (Day) | | 240 mg QD soft gelatin capsules (SGC) with a first 480 mg loading dose in TE patients | 240 mg QD solution (PiB) without a first 480 mg loading dose in TE patients |
|---|---|---|---|
| 4 | | 5,640 | 2,420 |
| 6 | | 7,060 | 2,950 |
| 10 | | 6,580 | 2,930 |
| 14 | | 5,590 | 2,850 |
| 21 | | 5,410 | 3,050 |
| 28 | | 5,960 | 4,210 |
| 29 | | 5,330 | 3,830 |
| Mean steady state trough of Days 10-29 | | 5,774 | 3,374 |
| % of mean steady state trough of Days 10-29 | 2 | 60.1 | 21.0 |
| | 3 | 81.2 | 49.2 |
| | 4 | 97.7 | 71.7 |
| | 6 | 122.3 | 87.4 |

Conclusion: By dosing with a loading dose administered for the first administration dose of the treatment, it is possible to achieve higher levels of active drug in the patient's body at an early stage of the treatment thus achieving plasma concentration levels that are closer to the steady state level (higher percentage of steady state level) at this early stage, as well as effectively achieve steady state levels of the active drug earlier than would otherwise be achieved without a loading dose.

Overall Assessment

These results demonstrate a strong and very rapid antiviral affect in treatment-naïve patients treated with Compound (1) sodium salt given once-daily as monotherapy for 14 days, which is followed by anti-viral resistance formation and increase in viral load after 5-6 days of monotherapy. Upon initiation of the triple combination therapy of the present invention at Day 14 (Compound (1) sodium salt, with pegylated interferon alfa 2a and ribavirin), however, viral load progressively decreased demonstrating the antiviral effectiveness of the triple combination therapy of the present invention in treatment-naïve patients. See FIG. 1.

When Compound (1) sodium salt was given once-daily to treatment-experienced patients (interferon plus ribavirin null responders and partial responders) in combination with pegylated interferon alfa 2a and ribavirin for 28 days, the results demonstrate the same strong and very rapid antiviral response but with reduced resistance formation. See FIG. 2. One would have expected in such treatment-experienced, non-responder patients that a similar viral resistance would have occurred after Day 5 as these patients were selected for being non-responsive to pegylated interferon plus ribavirin therapy. However, a continuous viral suppression occurred.

In essence, it has been shown that the triple combination therapy of the present invention can effectively reduce the viral load of treatment-naïve and treatment-experienced patients with chronic genotype-1 hepatitis C viral infection and, at least in some patients, keep it at less than detectable level, that is defined as below 50 International Units per ml serum of a patient as measured by quantitative, multi-cycle reverse transcriptase PCR methodology according to the WHO international standard. In preferred embodiments, the triple combination therapy of the present invention can effectively reduce the viral load in HCV genotype 1-infected patients to below 10 International Units per ml serum.

Additional clinical studies have been conducted with the triple combination therapy of the present invention and incorporating both the lead-in and loading dose concepts of the present invention, or just the loading dose concept, and have demonstrated similar effectiveness against genotype-1 hepatitis C viral infection with minimal viral rebound, in both treatment-naive and non-responder patients who have undergone previous interferon/ribavirin therapy. It has also been demonstrated that with the use of a loading dose one can achieve higher plasma levels of active agent more quickly and effectively shorten the time it takes for the patient to achieve steady state levels of the active in the blood. This effect should be of significant benefit in enabling the suppression of the emergence of viral resistance in the patient.

Definitely Surprising Results Include:

(1) no early resistance formation (e.g., variants encoding NS3 amino acid substitutions at R155 and/or D168) in treatment-experienced patients who are treated with Compound (1) sodium salt in combination with pegylated interferon alfa 2a and ribavirin at standard doses (FIG. 2) as compared to the effect of the same dose of Compound (1) sodium salt alone in treatment-naïve patients who experienced viral resistance (see FIG. 1, first 14 days). One would have expected in treatment experienced patients that a similar viral resistance would have occurred after Day 5 even with the addition of pegylated interferon alfa 2a and ribavirin as these patients were selected for being non-responsive to previous pegylated interferon plus ribavirin combination therapy; and (2) that a dose of only 120 mg QD (once daily) in combination with pegylated interferon and ribavirin induced a viral depletion to below the level of quantification (defined as less than 25 IU per ml of serum) in more than 50% of the treatment-experienced patients who have been previously non-responsive to pegylated interferon plus ribavirin therapy (see table).

Example 9

Methods for Identifying HCV NS3 Variants

Viral RNA Extraction and PCR Amplification

Viral RNA was isolated from plasma of HCV-infected subjects and a DNA fragment of 2.4 kbp containing the complete NS3-NS4A region was first synthesized using SUPERSCRIPT™ III one step RT-PCR System (Invitrogen) and two gene-specific primers spanning positions 3276 in NS2 and 5650 in NS4B. After purification of the first PCR product, two different second-round, semi-nested PCR products of either 2.3 or 0.7 kbp (spanning the entire NS3/NS4A or only the NS3 protease domain, respectively) were then generated using KOD Hot Start DNA polymerase (Novagen). The limit of detection of the RT-PCR amplification method restricted the analysis to patient samples with VL above 1000 IU/ml.

Sequence Analysis

The 2.3 kbp DNA product was then used for direct population-based sequencing of the entire NS3-NS4A 2055 nt region using BIG DYE® Terminator V3.1 (Applied Biosystems) and an ABI PRISM® 3130XL Genetic Analyzer (Applied Biosystems). Sequences were obtained from 10 primers to achieve at least 90% double strand coverage for the NS3-NS4A region. The resulting nucleotide sequences were analyzed with SEQSCAPE® v2.5 (Applied Biosystems).

The 0.7 kbp DNA fragment was used to generate the clonal-based (ZEROBLUNT® TOPO® Cloning Kit, Invitrogen) sequences of the 543 nt NS3 protease region covering the first 181 aa of NS3; for each sample 96 clones were picked and sequenced using universal primers with ABI PRISM® BIG DYE™ Terminator Cycle PCR Sequencing. Two single pass sequences were performed for each clone resulting in 90-100% double strand coverage of the 543 nt region analyzed with MUTATION SURVEYOR™ v3.0 (Softgenetics LLC). For each patient sample, the clones with low quality sequence or containing deletions, insertions or stop codons were not included for further analysis such that the number of clones analyzed varied from 74 to 89 (with a median and average of 80 clones).

The resulting sequences were compared to reference sequences according to their respective subtypes which were previously determined during the trial screening phase with the TRUEGENE™ HCV 5'NC genotyping assay. AF009606 served as the reference for subtype 1a and AJ238799 for subtype 1b. Particular attention was focused on mutations that resulted in amino acid substitutions at 15 positions in the NS3 protease domain. These positions were all previously reported as potentially conferring resistance to this class of compounds. These positions are: 36, 41, 54, 71, 80, 86, 89, 109, 111, 155, 156, 168, 170, 176 and 178 (References: [1] Tong X, Bogen S, Chase R, Girijavallabhan V, Guo Z, Njoroge F G, Prongay A, Saksena A, Skelton A, Xia E, Ralston R. Characterization of resistance mutations against HCV ketoamide protease inhibitors. Antiviral Res. 2008 March 77(3):177-185. [2.] Lagacé L, Marquis M, Bousquet C, Do F, Gingras R, Lamarre D, Lamarre L, Maurice R, Pause A, Pellerin C, Spickler C, Thieault D, and Kukolj G. BILN 2061 and beyond: pre-clinical evaluation of HCV subgenomic replicon resistance to a NS3 protease inhibitor. In Framing the Knowledge of Therapeutics for Viral Hepatitis. R F Schinazi and E R Schiff (eds). P 263-278 IHL press, 2006 [3.] Koev G, Kati W. The emerging field of drug resistance. Expert Opinion Invest Drugs 17(3), 303-319, 2008 (P08-03895)

Drug Sensitivity Assays

A bicistronic HCV replicon shuttle vector (pIT2) comprising a luciferase reporter gene and an adapted Con-1 NS3/NS5B region was modified to create two unique restriction sites (Mlu I and Spe I) at NS3 codons 11 and 225 which enabled the insertion of compatible NS3 amplicons isolated from HCV-infected patient plasma samples. The first-round PCR product synthesized from the patient plasma-purified RNA (also used for generating fragments for population- and clonal-based sequencing) was used to amplify a 0.65 kbp fragment with primer pairs that respectively contain the unique MluI and SpeI restriction sites for insertion into the shuttle vector. Amplicons were ligated in the pIT2 shuttle vector and reconstituted plasmid DNA was used to generate HCV subgenomic replicon RNA transcripts (T7 RIBOMAX™ kit, Promega). The in vitro transcribed RNA was transiently transfected by electroporation in Huh-7.5 cells which were then seeded in 96 well plates for 24 hours and treated with a range of Compound (1) sodium salt (or IFN-α) concentrations for a period of 72 hours. At the end of the incubation, luciferase activity was measured with the BRIGHT-GLO™ substrate as the luminescence quantified (CPS) in each well of the culture plate reflected the amount of HCV RNA replication. The level of inhibition (% inhibition) in each well containing inhibitor was calculated with the following equation: % inhibition=100−[100×CPS (inhibitor)/CPS (control)]. The concentration giving 50% inhibition of HCV RNA replication ($EC_{50}$) was determined by the non-linear regression routine NLIN procedure of SAS. The $EC_{50}$ of mutant NS3 were compared to the baseline $EC_{50}$ and used to generate fold-change values.

The predominant genotype 1a resistance mutations in on-treatment viral rebound samples encoded an R155K substitution, and other minor variants were detected by clonal sequence analysis at this position. R155K variants conferred reductions in sensitivity to Compound (1) with the range of $EC_{50}$ values of 1.8-6.5 μM. The genotype 1b viruses mainly encoded changes at D168, with valine as a predominant substitution, and other minor variants detected by sensitive clonal sequencing. $EC_{50}$ values for D168 variants ranged 3.6-15 μM. This profile may be attributable, in part, to a different mutational barrier to resistance at the R155 codon in genotype 1a (a single nucleotide transition changes the codon to a lysine) versus genotype 1b (that requires two nucleotide substitutions to encode a change to lysine.

The invention claimed is:

1. A method of treating hepatitis C viral (HCV) infection in a patient comprising administering to the patient a therapeutic combination comprising:
   (a) Compound (1) or a pharmaceutically acceptable salt thereof:

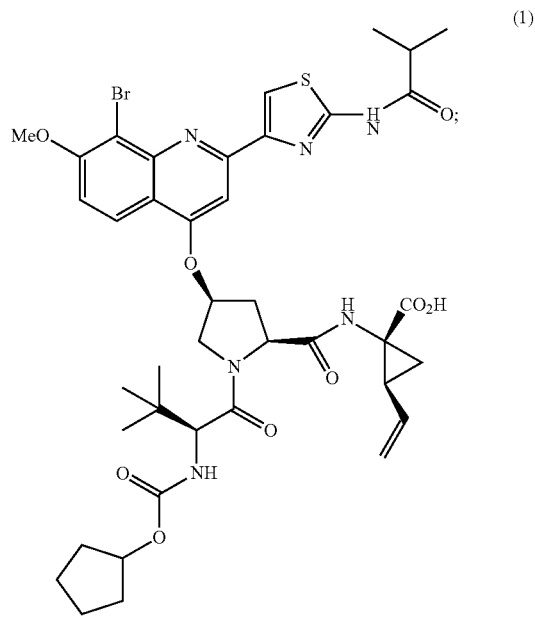 [SMILES: C=C[C@@H]1C[C@]1(NC(=O)[C@@H]1C[C@H](Oc2cc(-c3csc(NC(=O)C(C)C)n3)nc3c(Br)c(OC)ccc23)CN1C(=O)[C@@H](NC(=O)OC1CCCC1)C(C)(C)C)C(=O)O]

(b) an interferon alpha; and
   (c) ribavirin;
   wherein the first dose of Compound (1), or a pharmaceutically acceptable salt thereof, that is administered to the patient is double in quantity by weight to the subsequent doses thereof and wherein Compound (1), or a pharmaceutically acceptable salt thereof, is administered at a dosage of about 240 mg to about 480 mg in the first dose, and at a dosage of about 120 mg to about 240 mg in subsequent doses.

2. A method according to claim 1, wherein Compound (1), or a pharmaceutically acceptable salt thereof, is administered at a dosage of about 240 mg in the first dose, and at a dosage of about 120 mg in subsequent doses.

3. A method according to claim 1, wherein Compound (1), or a pharmaceutically acceptable salt thereof, is administered at a dosage of about 480 mg in the first dose, and at a dosage of about 240 mg in subsequent doses.

4. The method according to claim 1, wherein the HCV infection is genotype 1.

5. The method according to claim 1, wherein said patient is a treatment-naive patient.

6. The method according to claim 1, wherein said patient is non-responsive to a combination therapy using ribavirin and an interferon alpha.

7. The method according to claim 1, wherein said interferon alpha is a pegylated interferon alfa.

8. The method according to claim 1, wherein said interferon alfa is pegylated interferon alfa-2a or pegylated interferon alfa-2b.

9. The method according to claim 1, wherein on the first day of treatment with Compound (1), or a pharmaceutically acceptable salt thereof, the Compound (1), or a pharmaceutically acceptable salt thereof, is administered at a dose of 480 mg and on subsequent days at a dose of 240 mg per day.

10. The method according to claim 1, wherein on the first day of treatment with Compound (1), or a pharmaceutically acceptable salt thereof, the Compound (1), or a pharmaceutically acceptable salt thereof, is administered at an initial dose of 480 mg and at subsequent doses of 240 mg twice per day.

11. The method according to claim 1, wherein on the first day of treatment with Compound (1), or a pharmaceutically acceptable salt thereof, the Compound (1), or a pharmaceutically acceptable salt thereof, is administered at a dose of 240 mg and on subsequent days at a dose of 120 mg per day.

* * * * *